US006960465B1

(12) United States Patent
Papoutsakis et al.

(10) Patent No.: US 6,960,465 B1
(45) Date of Patent: Nov. 1, 2005

(54) INCREASED CELL RESISTANCE TO TOXIC ORGANIC SUBSTANCES

(75) Inventors: Eleftherios T. Papoutsakis, Glenview, IL (US); Christopher A. Tomas, Niles, IL (US); Marija Tesic, Evanston, IL (US); Jose Y. Santiago, Chicago, IL (US)

(73) Assignee: Northwestern University, Evanston, IL (US)

( * ) Notice: Subject to any disclaimer, the term of this patent is extended or adjusted under 35 U.S.C. 154(b) by 10 days.

(21) Appl. No.: 10/186,335

(22) Filed: Jun. 27, 2002

Related U.S. Application Data

(60) Provisional application No. 60/301,353, filed on Jun. 27, 2001.

(51) Int. Cl.$^7$ ................................ C12N 1/00; C12P 1/00
(52) U.S. Cl. ...................... 435/252.3; 435/41; 435/128; 435/132; 435/170; 435/171; 435/252.7; 435/252.9
(58) Field of Search .......................... 435/41, 128, 171, 435/132, 170

(56) References Cited

U.S. PATENT DOCUMENTS 6,156,532 A * 12/2000 Kimura et al. ................. 435/41
6,159,708 A * 12/2000 Sogo et al. ................. 435/69.1

OTHER PUBLICATIONS

Pich, A., F. Narberhaus, and H. Bahl. 1990 Appl. Microbiol. Biotechnol. 33:697–704.*
Walter, K.A., L.D. Mermelstein, and E.T. Papoutsakis. 1994 FEMS Microbiol. Lett. 123:335–342.*
Kalbach, C.E., and Gatenby, A.A. 1993 Ezyme Microb. Technol. 15(9): 730–735.*
Mizunoe, Y., Wai, S., Umene, K., Kokubo, T., Kawabata, S., and Yoshida, S. 1999 Microbiol. Immunol. 43(6):513–520.*
Tomas, C., Welker, N., Papoutsakis, E. 2003 Appl. and Environ. Microbiol. 69(8): 4951–4965.*
Aono, R., Improvement of Organic Solvent Tolerance Level of *Escherichia coli* by Overexpression of Stress– Responsive Genes, Extremophiles, 1998, 2:239–248.
Asako, H., Nakajima, H., Kobayashi, K., Kobayaski, M., and Aono, R., Organic Solvent Tolerance and Antiobiotic Resistance Increased by Overexpression of *marA* in *Escherichia coli*, Applied and Environmental Microbiology, Apr. 1997, p. 1428–1433.
Bahl, H., Muller, H., Behrens, S., Joseph, H., and Narberhaus, F., Expression of Heat Shock Genes in *Clostridium acetobutylicum*, FEMS Microbiology Reviews 17, 1995, p. 341–348.
Bahl, H., Chapter 11: Heat Shock Response and Onset of Solvent Formation in *Clostridium acetobutylicum*, The Clostridia and Biotechnology, D.R. Woods, Editor, 1993, p. 247–259.

Bukau, B., and Walker, G. Cellular Defects Caused by Deletion of the *Escherichia coli dnaK*Gene Indicate Roles for Heat Shock Protein in Normal Metabolism, Journal of Bacteriology, May 1989, p. 2337–2346.
Kieboom, J., Dennis, J., de Bont, J., and Zylstra, G., Identification and Molecular Characterization of an Efflux Pump Involved in *Pseudomonas putida* S12 Solvent Tolerance, The Journal of Biological Chemistry, Jan., 1998, vol. 273, No. 1, p. 85–91.
Li, X, Zhang, L., and Poole, K., Role of the Multidrug Efflux Systems of *Pseudomonas aeruginosa* in Organic Solvent Tolerance, Journal of Bacteriology, Jun. 1998, p. 2987–2991.
Nishihara, K., Kanemori, M., Kitagawa, M., Yanagi, H., and Yura, T., Chaperone Coexpression Plasmids: Differential and Synergistic Roles of DnaK–DnaJ–GrpE and GroEL–GroES in Assisting Folding of an Allergen of Japanese Cedar Pollen, Cryj2, in *Escherichia coli*, Applied and Environmental Microbiology, May 1998, p. 1694–1699.
Pich., A, Narberhaus, F., and Bahl, H., Induction of Heat Shock Proteins During Initiation of Solvent Formation in *Clostridium acetobutylicum*, Appl. Microbiol. Biotechnol. 1990, 33:697–704.
Volker, U., Mach, H., Schmid, R., and Hecker, M., Stress proteins and cross–protection by heat shock and salt stress in *Bacillus subtilis*, Journal of General Microbiology, 1992, 138, 2125–2135.
White, D., Goldman, J., Demple, B., and Levy, S., Role of the *acrAB* Locus in Organic Solvent Tolerance Mediated by Expression of *marA*, *soxS*, or *robA* in *Escherichia coli*, Journal of Bacteriology, Oct. 1997, p. 6122–6126.
Wu, S., Ye, R., Wu, X, Ng, S., and Wong, S., Enhanced Secretory Production of a Single–Chain Antibody Fragment from *Bacillus subtilis* by Coproduction of Molecular Chaperones, Journal of Bacteriology, Jun. 1998, p. 2830–2835.
Soucaille, P., Joliff, G., Izard, A., and Goma, G., Butanol Tolerance and Autobacteriocin Production by *Clostridium acetobutylicum*, Current Microbiology, vol. 14, 1987, p. 295–299.
Yura, T., and Nakahigashi, K., Regulation of the Heat–Shock Response, Current Opinion in Microbiology, 1999, 2:153–158.
Zuber, U., and Schumann, W., Circe, a Novel Heat Shock Element Involved in Regulation of Heat Shock Operon *dnaK* of *Bacillus subtilis*, Journal of Bacteriology, Mar. 1994, p. 1359–1363.

(Continued)

*Primary Examiner*—Karen Cochrane Carlson
*Assistant Examiner*—Anand Desai
(74) *Attorney, Agent, or Firm*—Reinhart Boerner Van Deuren s.c.

(57) ABSTRACT

Recombinant microorganisms and related methods of use to enhance tolerance to toxic substances. In particular, such microorganisms and methods can be used to increase solvent production.

23 Claims, 3 Drawing Sheets

OTHER PUBLICATIONS

Mizunoe, Y., Wai, S., Umene, K., Kokubo, T., Kawabata, S., and Yoshida, S., Cloning, Sequencing, and Functional Expression in *Escherichia coli* of Chaperonin (*groESL*) Genes from *Vibrio cholerae*, Microbiol. Immunol., 1999, 43(6), p. 513–520.

Walter, K., Mermelstein, L., and Papoutsakis, E., Host–Plasmid Interactions in Recombinant Strains of *Clostridium acetobutylicum* ATCC 824, FEMS Microbiology Letters 123, 1994, p. 335–342.

Kalbach, C., and Gatenby, A., Stable Expression Plasmid for High–Level Production of GroE Molecular Chaperones in Large–Scale Cultures, Enzyme Microb. Technol., 1993, vol. 15, p. 730–735.

Tomas, C., Welker, N., and Papoutsakis, E., Overexpression of *groESL* in *Clostridium acetobutylicum* Results in Increased Solvent Production and Tolerance, Prolonged Metabolism, and Changes in the Cell's Transcriptional Program, Applied and Environmental Microbiology, Aug. 2003, p. 4951–4965.

* cited by examiner

INCREASED CELL RESISTANCE TO TOXIC ORGANIC SUBSTANCES

This application claims priority benefit from pending U.S. provisional application Ser. No. 60/301,353, filed on Jun. 27, 2001, the entirety of which is incorporated herein by reference.

The United States government has certain rights to this invention pursuant to Grant Nos. BES-9632217 and BES-9911231 from The National Science Foundation and R-82856201-0 from the Environmental Protection Agency to Northwestern University.

BACKGROUND OF THE INVENTION

A wide variety of commercially important commodity or specialty chemicals are produced through metabolic engineering, the manipulation of living organisms to achieve desirable metabolic substrates, products and/or byproducts. The advent of recombinant DNA technology has enabled metabolic pathway modification using targeted genetic modifications instead of and/or in addition to the traditional mutagenesis and selection approach. Since the mid 1980s, numerous examples of metabolic engineering have been reported. In addition to manipulating the genetic code, variables such as temperature and aerobic conditions can also be engineered or manipulated to achieve the desired results. One of the major limitations in such bio-production processes is the toxic effect of many of the desired substrates, products and/or byproducts. This is a problem of both specific and general significance because it is encountered in the production of commodity chemicals from renewable sources, bioremediation technologies, and the use of cells in biocatalysis involving toxic organic molecules.

The strictly anaerobic, Gram-positive, solventogenic clostridia (*C. acetobutylicum, C. beijerinckii* and related species) are excellent candidates for generating metabolically engineered strains for several potential applications. The fermentation byproducts of these species may lead to industrial processes for production of butanol, butyric acid, acetone, butanediol, propanol, 1,3-propanediol, polysaccharides, and enzymes, or for biotransformations and bioremediation. For example, *clostridia* grow under a low redox potential, enabling a variety of stereospecific reductions yielding chiral products that are difficult to synthesize chemically. In addition, these and related clostridial species can degrade a number of toxic chemicals and are thus good candidates for bioremediation applications. A major advantage of solventogenic *clostridia* is their ability to utilize an unusually large variety of substrates: mono-, oligo- and poly-saccharides, including the most common pentoses and hexoses, and as such to utilize biomass hydrolysates.

Important potential applications of solventogenic *clostridia* include production of butanol and acetone. However, such production is affected by poor process economics; for example, a typically low butanol titer in the product stream. Low butanol titers are due to the low tolerance of these organisms to butanol, with final butanol concentrations rarely exceeding 12–13 g/l. As a result, butanol separation costs are high. Economic analyses show that if the final butanol concentration was raised from 12 to 19 g/l, the separation costs would be cut in half.

As mentioned above, butanol toxicity is quite severe. Butanol concentration in the final product stream usually cannot exceed 12–13 g/l, before cellular degradation. At high concentrations, butanol inhibits active nutrient transport, membrane bound ATPase, glucose uptake, partially or completely abolishes the membrane $\Delta pH$ and $\Delta \psi$, and lowers the intracellular pH. To date, butanol toxicity has been attributed to its chaotropic effect on the cell membrane. However, the membrane model may not afford a complete explanation for butanol toxicity, as a *clostridia* strain with the inactive buk gene produces 230 mM (17 g/l) butanol, 83 mM (4.8 g/l) acetone and 69 mM (3.2 g/l) ethanol (total solvents of 25 g/l) [Harris, L. M., Desai, R. P., Welker, N. E., Papoutsakis, E. T. "Characterization of recombinant strains of the *Clostridium acetobutylicum* butyrate kinase inactivation mutant: need for new phenomenological models for solventogenesis and butanol inhibition?", *Biotechnol. Bioeng.*, 67: 1–11 (2000)]. This strain overcame the 12–13 g/l butanol-toxicity limit without any specific selection or adaptation for increased butanol tolerance.

Stress-response proteins are a collection of specialized proteins that are essential to cellular function and are present in non-stressed cells under normal growth conditions, playing an important role in cell physiology as a protective cellular response to environmental stress. A common family of these stress response proteins are termed heat shock proteins (HSPs) due to their abundance following heat shock. The stress response proteins bind normative states of other proteins and assist in proper folding by recognizing exposed hydrophobic surfaces on normative protein species, which ultimately end up buried when the protein is in its properly folded, functional state. Generally, stress response proteins form noncovalent interactions with the hydrophobic regions of misfolded proteins, thereby stabilizing them from irreversible multimeric aggregation, misfolding of nascent polypeptides, unfolding during exposure to stress and eventual degradation. The stabilized and properly folded proteins are therefore available to perform their cellular function(s).

The major heat shock protein classes are the 90-kDa heat shock protein (HSP90), the 60-kDa heat shock protein (HSP60; including GroEL), the 70-kDa heat shock protein (HSP70; DnaK in *E. coli*) and 40-kDa heat shock protein (HSP40 or the DnaJ family). Another important protein involved in the heat shock response is a co-chaperone of HSP60 called chaperonin 10 (cpn10; GroES in *E. coli*).

DnaK operates by binding to nascent polypeptide chains on ribosomes, preventing premature folding, misfolding, or aggregation. DnaK is composed of two major functional domains. The $NH_2$-terminal ATPase domain and the COOH-terminal domain. The $NH_2$-terminal ATPase domain binds ADP and ATP and hydrolyzes ATP, whereas the COOH-terminal domain is responsible for polypeptide binding. DnaJ is a co-chaperone for DnaK. GrpE is another chaperone involved in the DnaKJ folding pathway by facilitating the exchange between ADP and ATP. The genes for DnaK, DnaJ and GrpE are organized as an operon (the dnaK operon).

Another class of HSPs is the GroEL/ES family of proteins that bind partially folded intermediates, preventing their aggregation, and facilitating folding and assembly. In addition, it has been suggested that GroEL, with the assistance of its co-chaperonin GroES, may allow misfolded structures to unfold and refold. The GroEL of *E. coli* consists of 14 identical subunits in two-stacked heptameric rings, each containing a central cavity. The size of the GroEL/ES complex cavity suggests that proteins of up to 50–60 kDa can be handled by this chaperone system. The genes for GroEL/ES are also organized as an operon (the groE operon). In *B. subtilis*, expression of the dnaK and groE operons is negatively regulated by a repressor protein through a CIRCE DNA element (a palindromic sequence between the promoter and the initiation codon). For example, in *B. subtilis* inactivation of this repressor protein (HrcA)—whose activity is modulated by GroEL/ES—results in constitutive expression of the two HSP operons, and this enhances the folding and secretory production of proteins which are difficult to fold.

HSPs have also been detected in solventogenic *clostridia*. Terracciano, et al. showed that a moderate increase in butanol concentration can cause a response in *C. acetobutylicum* similar to that obtained from heat shock. Using a chemostat, Pich, et al. demonstrated that the synthesis rates of HSPs, as well as solventogenic proteins, increased several hours before solvents were detected in the medium. It was also noted by Bahl that some of the factors necessary for the initiation of solventogenesis in *C. acetobutylicum* may also be responsible for the induction of stress response, namely lowered pH, low growth rate, and excess carbohydrates.

The preceding studies only allude to the presence of heat/shock stress response proteins in solventogenic bacteria, but without conclusive evidence regarding the role of such proteins or guidance as to their use in solvent production. The viability of solventogenic bacteria has been a long-standing, unresolved concern of the prior art. There remains a need in the art to provide an organism and/or related method to enhance fermentation by such bacteria and increase solvent production.

The foregoing background information, together with other aspects of the prior art, is described more fully and better understood in light of the following publications.

1. Ahmed, M., C. M. Borsch, S. S. Taylor, N. Vazquez-Laslop, and A. A. Neyfakh, *A protein that activates expression of a multidrug efflux transporter upon binding the transporter substrates*. J Biol Chem, 1994. 269(45): p. 28506–28513.
2. Ahmed, M. L. Lyass, P. N. Markham, S. S. Taylor, N. Vazquez-Laslop, and A. A. Neyfakh, *Two highly similar multidrug transporters of Bacillus subtilis whose expression is differentially regulated*. J Bacteriol, 1995. 177(14): p. 3904–3910.
3. Altschul, S. F., T. L. Madden, A. A. Schaffer, J. Zhang, Z. Zhang, W. Miller, and D. J. Lipman, *Gapped BLAST and PSI-BLAST: a new generation of protein database search programs*. Nucleic Acids Res., 1997. 25(17): p. 3389–3402.
4. Aono, R., *Improvement of organic solvent tolerance level of Escherichia coli by overexpression of stress-responsive genes*. Extremophiles, 1998: 2(3): p. 239–248.
5. Aono, R., M. Kobayashi, H. Nakajima, and H. Kobayashi, *A close correlation between improvement of organic solvent tolerance levels and alteration of resistance toward low levels of multiple antibiotics in Escherichia coli*. Biosci Biotechnol Biochem, 1995. 59(2): p. 213–218:
6. Arnosti, D. N., V. L. Singer, and M. J. Chamberlin, *Characterization of heat shock in Bacillus subtilis*. J Bacteriol, 1986. 168(3): p. 1243–1249.
7. Asako. H., H. Nakajima, K. Kobayashi, M. Kobayashi, and R. Aono, *Organic solvent tolerance, and antibiotic resistance increased by overexpression of marA in Escherichia coli*. Appl Environ Microbiol, 1997: 63(4): p. 1428–1433.
8. Bahl, H., Chapter 11: *Heat Shock Response and Onset of Solvent Formation in Clostridium acetobutylicum*, in *The Clostridia and Biotechnology*, D. R. Woods, Editor. 1993, Butterworth-Heinemann: Boston. p. 247–259.
9. Bahl, H. and G. Gottschalk, in *Biotechnology*, H. J. Rehm and G. Reed, Editors. 1988, VCH Verlagsgesellschaft. p. 1–30.
10. Bahl, H. H. Muller, S. Behrens, H. Joseph, and F. Narberhaus, *Expression of heat shock genes in Clostridium acetobutylicum*. FEMS Microbiology Reviews, 1995. 17(3): p. 341–348.
11. Bailey, J: E., *Toward a science of metabolic engineering*. [*Review*]. Science, 1991. 252: p. 1668–1675.
12. Baneyx, F. and G. Georgiou, *Construction and characterization of Escherichia coli strains deficient in multiple secreted proteases: protease III degrades high-molecular-weight substrates in vivo*. J. Bacteriol, 1991. 173(8): p. 2696 2703.
13. Bennett, G. N. and D. J. Petersen, *Cloning and expression of Clostridium acetobutylicum genes involved in solvent production*, in *Genetics and Molecular Biology of Anaerobes*, M. Sebald, Editor. 1993, Springer-Verlag: New York. p. 317–343.
14. Blaschek, H. P. and B. A. White, *Genetic systems development in clostridia*. FEMS Microbiology Reviews, 1995. 17: p. 349–356.
15. Borys, M. C., D. I. Linzer, and E. T. Papoutsakis, *Culture pH affects expression rates and glycosylation of recombinant mouse placental lactogen proteins by Chinese hamster ovary (CHO) cells*. Biotechnology, (NY), 1993. 11(6): p. 720–724.
16. Bowles, L. K: and W. L. Ellefson, *Effects of butanol on Clostridium acetobutylicum*. Appl Environ Microbiol, 1985. 50(5): p. 1165–1170.
17. Bukau, B. and G. C. Walker, *Cellular defects caused by deletion of the Escherichia coli dnaK gene indicate roles for heat shock protein in normal metabolism*. J Bacteriol, 1989. 171(5): p. 2337–2346.
18. Cameron, D. C. and I. T. Tong, *Cellular and metabolic engineering. An overview.* [*Review*]. Applied Biochemistry and Biotechnology, 1993. 38(1–2): p. 105–140.
19. Chen, J. S., *Alcohol dehydrogenase: multiplicity and relatedness in the solvent producing clostridia*. FEMS Microbiology Reviews, 1995. 17(3): p. 263–274.:
20. Cornillot, E., Soucaille, P., *Solvent forming genes in Clostridia*. Nature, 1996. 380: p. 489.
21. Comillot, E. C. Croux, and P. Soucaille, *Physical and genetic map of the Clostridium acetobutylicum ATCC 824 chromosome*. J. Bacteriol, 1997. 179(23): p. 7426–7434.
22. Cornillot, E., R. V. Nair, E. T. Papoutsakis, and P. Soucaille, *The genes for butanol and acetone formation in Clostridium acetobutylicum ATCC 824 reside on a large plasmid whose loss leads to degeneration of the strain*. J Bacteriol, 1997. 179(17): p. 5442–5447.
23. Dadgar, A. M. and G. L. Foutch, *Improving the acetone-butanol fermentation process with liquid—liquid extraction*. Biotechnology Progress, 1988. 4: p. 36–39.
24. Desai, R. P., L. M. Harris, N. E. Welker, and E. T. Papoutsakis, *Metabolic flux analysis elucidates the importance of the acid-forniation pathways in regulating solvent production by Clostridium acetobutylicum*. Metabolic Engineering, 1999-accepted.
25. Desai, R. P., L. N. Nielsen, and E. T. Papoutsakis, *Metabolic flux analysis of C. acetobutylicum fermentations. using nonlinear constraints*. Journal of Biotechnology, 1999. 71: p. 191–205.
26. Desai, R. P. and E. T. Papoutsakis, *Antisense RNA strategies for the metabolic engineering of Clostridium acetobutylicum*. Applied and Environmental Microbiology, 1999. 65(3): p. 936–945.
27. Dower, W. J., B. M. Chassy, J. T. Trevors, arid H. P. Blaschek, in *Handbook of Electroporation*, A. C. Y. Chang, Editor. 1992, Academic Press: New York. p. 485–498.

28. Durre, P., *New, insights and novel developments in clostridial acetone/butanol/isopropanol fermentation.* Appl Microbiol Biotechnol, 1998. 49(6): p. 639–648.
29. Eremeeva, M. E., W. M. Ching, Y. Wu, D. J. Silverman, and GA. Dasch, *Western blotting analysis of heat shock proteins of Rickettsiales and other eubacteria.* FEMS Microbiol Lett, 1998. 167(2): p. 229–237.
30. Fink, A. L., *Chaperone-mediated protein folding.* Physiol Rev, 1999. 79(2): p. 425–449.
31. Fischer, R. J., J. Helms, and P. Durre, *Cloning, sequencing, and molecular analysis of the sol operon of Clostridium acetobutylicum, a chromosomal locus involved in solventogenesis.* J Bacteriol, 1993. 175(21): p. 6959–6969.
32. Francis, A. J. and C. J. Dodge, *Dissolution of Ferrites by Clostridum-SP.* Geomicrobiology Journal, 1991. 9(1): p. 27–40.
33. Francis, A. J., C. J. Dodge, F. L. Lu, G. P. Halada, and C. R. Clayton, *XPS and Xanes Studies of Uranium Reduction by Clostridium SP.* Environmental Science & Technology, 1994. 28(4): p. 636–639.
34. Gerischer, U. and P. Durre, *Cloning, sequencing, and molecular analysis of the acetoacetate decarboxylase gene region from Clostridium acetobutylicum.* J Bacteriol, 1990. 172(12): p. 6907–6918.
35. Gerischer, U. and P. Durre, *mRNA analysis of the adc gene region of Clostridium acetobutylicum during the shift to solventogenesis.* J Bacteriol, 1992. 174(2): p. 426–433.
36. Girbal, L. and P. Soucaille, *Regulation of solvent production in Clostridium acetobutylicum.* Trends in Biotechnology, 1998. 16: p. 11–16.
37. Gottwald, M. and G. Gottschalk, *The internal pH of Clostridium acetobutylicum and its effect on the shift from acid to solvent formation.* Archives of Microbiology, 1985. 143: p. 42–46.
38. Green, E. M. and G. N. Bennett, *Inactivation of an aldehyde/alcohol dehydrogenase gene from Clostridium acetobutylicum ATCC 824.* Appl Biochem Biotechnol, 1996. 57–58: p. 213–221.
39. Green, E. M., Z. L. Boynton, L. M. Harris, F. B. Rudolph, E. T. Papoutsakis, and G. N. Bennett, *Genetic manipulation of acid formation pathways by gene inactivation in Clostridium acetobutylicum ATCC 824.* Microbiology, 1996. 142(Pt 8): p. 2079–2086.
40. Harris, L. (1997). *Fermentation characterization of Clostridium acetobutylicum ATCC 824 recombinant strains.* M.S. thesis, Chemical Engineering, Northwestern University, Evanston.
41. Herbort, M., U. Schon, K. Angermann, J. Lang, and W. Schumann, *Cloning and sequencing of the dnaK operon of Bacillus stearothermophilus.* Gene, 1996. 170(1): p. 81–84.
42. Hermann, M., F. Fayolle, R. Marchal, L. Podvin, M. Sebald, and J. P. Vandecasteele, *Isolation and characterization of butanol-resistant mutants of Clostridium acetobutylicum.* Appl Environ Microbiol, 1985. 50(5): p. 1238–243.
43. Hirayarna, H., H. Takami, A. Inoue, and K. Horikoshi, *Isolation and characterization of toluene-sensitive mutants from Pseudomonas putida IH-2000.* FEMS Microbiol Lett, 1998. 169(2): p. 219–225.
44. Huang, L., C. W. Forsberg, and L. N. Gibbens, *Influence of external pH and fermentation products on Clostridium acetobutylicum intracellular pH and cellular distribution of fermentation products.* Applied and Environmental Microbiology, 1986. 51: p. 1230–1234.
45. Hughes, J. B., C. Y. Wang, R. Bhadra, A. Richardson, G. N. Bennett, and F. B. Rudolph, *Reduction of 2,4,6-trinitrotoluene by Clostridium acetobutylicum through hydroxylamirio-nitrotoluene intermediates.* Environmental Toxicology and Chemistry, 1998. 17(3): p. 343–348.
46. Hüsemann, M. H. W. and E. T. Papoutsakis, *Solventogenesis in Clostridium acetobutylicum fermentations related to carboxylic-acid and proton concentrations.* Biotechnology and Bioengineering, 1988. 32: p. 843–852.
47. Johnson, J. L., J. Toth, S. Santiwatanakul, and J. S. Chen, *Cultures of "Clostridium acetobutylicum" from various collections comprise Clostridium acetobutylicum, Clostridium beijerinckii, and two other distinct types based on DNA—DNA reassociation.* International Journal of Systematic Bacteriology, 1997. 47(2): p. 420–424.
48. Jones, D. T. and D. R. Woods, *Acetone-butanol fermentation revisited.* Microbiological Reviews, 1986. 50: p. 484–524.
49. Jones, D. T. and D. R. Woods, in *Clostridia*, N. P. Minton and D. J. Clarke, Editors. 1989, Plenum Press: New York. p. 105–144.
50. Keis, S., C. F. Bennett, V. K. Ward, and D. T. Jones, *Taxonomy and phylogeny of industrial solvent-producing clostridia.* International Journal of Systematic Bacteriology, 1995. 45(4): p. 693–705.
51. Kieboom, J., J. J. Dennis, J. A. de Bont, and G. J. Zylstra, *Identification and molecular characterization of an efflux pump involved in Pseudomonas putida S12 solvent tolerance.* J Biol Chem, 1998. 273(1): p. 85–91.
52. Kim, B. H., P. Bellows, R. Datta, and J. G. Zeikus, *Control of carbon and electron flow in Clostridium acetobutylicum fermentation: Utilization of carbon monoxide to inhibit hydrogen production and to enhance butanol yields.* Applied and Environmental Microbiology, 1984. 48: p. 764–770.
53. Lee, S. Y., G. N. Bennett, and E. T. Papoutsakis, *Construction of Escherichia coli-Clostridium acetobutylicum Shuttle Vectors and Transformation of Clostridium acetobutylicum Strains.* Biotechnology Letters, 1992. 14: p. 427–432.
54. Lee, S. Y., L. D. Mermelstein, G. N. Bennett, and E. T. Papoutsakis, *Vector construction, transformation, and gene amplification in Clostridium acetobutylicum ATCC 824.* Ann N Y Acad Sci, 1992. 665: p. 39–51.
55. Lee, S. Y., L. D. Mermelstein, and E. T. Papoutsakis, *Determination of plasmid copy number and stability in Clostridium acetobutylicum ATCC 824:* FEMS Microbiol Lett, 1993. 108(3): p: 319–323:
56. Lee, S. Y. and E. T. Papoutsakis (Editors), *Metabolic Engineering.* 1999, New York, N.Y.: Marcel Dekker.
57. Lenz, T. G. and A. R. Moreira, *Economic evaluation of the acetone-butanol fermentation.* Ind Eng. Chem Prod Res Dev, 1980. 19: p. 478–483.
58. Li, M. and S. L. Wong, *Cloning and characterization of the groESL operon from Bacillus subtilis.* J Bacteriol, 1992. 174(12): p. 3981–3992.
59. Li, X. Z., L. Zhang, and K. Poole, *Role of the multidrug efflux systems of Pseudomonas aeruginosa in organic solvent tolerance.* J. Bacteriol, 1998. 180(11): p. 2987–2991.
60. Linden, J. C. and R. H. Kuhn, *Biochemistry of alcohol effects on clostridia,* in *Alcohol toxicity in yeasts and bacteria,* N. van Uden, Editor. 1989, CRC Press: Boca Raton, Fla. p. 300.
61. Linden, J. C., A. R. Moreira, and T. G. Lenz, *Acetone and butanol,* in *Comprehensive biotechnology: The principles, applications, and regulations of biotechnology*

61. *in industry, agriculture, and medicine*, M. Moo-Young, et al, Editors. 1985, Pergamon Press: New York. p. 15–930.
62. Marlatt, J. A. and R. Datta *Acetone-butanol fermentation process development and economic evaluation*. Biotechnology Progress, 1986. 2: p. 23–28.
63. McDowell, C. L. and E. T. Papoutsakis, *Increased agitation intensity increases CD13 receptor surface content and mRNA levels, and alters the metabolism of HL60 cells cultured in stirred tank bioreactors*. Biotechnol Bioeng, 1998. 60(2): p. 239–250.
64. McNeil, B., *The acetone butanol fermentation*. Adv Appl Microbiol, 1986. 31: p. 61–92:
65. Meinboth, J. and G. Wahl, *Hybridization of nucleic acids immobilized on solid supports*. Anal Biochem, 1984. 138(2): p. 267–284.
66. Mermelstein, L. D., Papoutsakis, E. T., Petersen, D. J., Bennett, G. N., *Metabolic engineering of Clostridium acetobutylicum ATCC 824 for increased solvent formation by enhancement of acetone formation enzyme activities using a synthetic acetone operon*. Biotechnology and Bioengineering, 1993. 42: p 1053–1060.
67. Mermelsteiri, L. D. and E. T. Papoutsakis, *In vivo methylation in Escherichia coli by the Bacillus subtilis phage phi 3T I methyltransferase to protect plasmids from restriction upon transformation of Clostridium acetobutylicum ATCC 824*. Appl Environ Microbiol, 1993. 59(4): p. 1077–1081.
68. Mermelstein, L. D., N. E. Welker, G. N. Bennett and E. T. Papoutsalcis, *Expression of cloned homologous fermentative genes in Clostridium acetobutylicum ATCC 824*. Biotechnology (NY), 1992. 10(2): p. 190–195.
69. Mogk, A. and W. Schumann, *Cloning and sequencing of the hrcA gene of Bacillus stearothermophilus*. Gene, 1997. 194(1): p. 133–136:
70. Nair, R. V., G. N. Bennett, and E. T. Papoutsakis, *Molecular characterization of an aldehydelalcohol dehydrogenase gene from Clostridium acetobutylicum ATCC 824*. J Bacteriol; 1994. 176(3): p. 871–885.
71. Nair, R. V., E. M. Green, D. E. Watson, G. N. Bennett, and E. T. Papoutsakis, *Regulation of the sol locus genes for butanol and acetone formation in Clostridium acetobutylicum ATCC 824 by a putative transcriptional repressor*. J Bacteriol, 1999. 181: p. 319–330.
72. Nair, R. V. and E. T. Papoutsakis, *Expression of plasmid-encoded aad in Clostridium acetobutylicum M5 restores vigorous butanol production*. J Bacteriol, 1994. 176(18): p. 5843–5846:
73. Narberhaus, F. and H. Bahl, *Cloning, sequencing, and molecular analysis of the groESL operon of Clostridium acetobutylicum*: J Bacteriol, 1992. 174(10): p. 3282–3289.
74. Narberhaus, F., K. Giebeler, and H. Bahl, *Molecular characterization of the dnaK gene region of Clostridium acetobutylicum, including grpE, dnaJ, and a new heat shock gene*. J Bacteriol, 1992: 174(10): p. 3290–3299.
75. Nishihara, K., M. Kanemori, M. Kitagawa, H. Yanagi, and T. Yura, *haperone coexpression plasmids: differential and synergistic roles of DnaK-Dnaj-GrpE and GroEL-GroES in assisting folding of an allergen of Japanese cedar pollen, Cryj2, in Escherichia coli*. Appl Environ Miciobiol, 1998: 64(5): p. 1694–1699:
76. Oethinger, M. I., I. Podglajen, W. V. Kern, and S. B. Levy, *Overexpression of the marA or soxS regulatory gene in clinical topoisomerase mutants of Escherzchia coli*. Antimicrob Agents. Chemother, 1998: 42(8): p. 2089–2094.
77. Ogden, R. C. and D. A. Adams, *Electrophoresis in agarose and acrylamide gels, in Guide to molecular cloning techniques*, S. L. Berger and A. R. Kimmel, Editors. 1987, Academic Press, Inc.: San Diego, Calif. p. 61–87.
78. Papoutsakis, E. T., *Equations and calculations for fermentations of butyric acid bacteria*. Biotechnology and Bioengineering, 1984. 26: p. 174–187.
79. Papoutsakis, E. T. and G. N. Bennett, *Cloning, structure, and expression of acid and solvent pathway genes of Clostridium acetobutylicum*. Chp. 8 in: *The Clostridia & Biotechnology*, D. R. Woods, Editor, Butterworth-Heinemann, Boston, Mass., 1993. p. 157–199.
80. Petersen, D. J: and G. N. Bennett, *Purification of acetoacetate decarboxylase from Clostridium acetobutylicum ATCC 824 and cloning of the acetoacetate decarboxylase gene in Escherichia coli*. Appl Environ Microbiol, 1990. 56(11): p. 3491–3498.
81. Petersen, D. J., J. W. Cary, J. Vanderleyden, and G. N. Bennett, *Sequence and arrangement of genes encoding enzymes of the acetone production pathway of Clostridium acetobutylicum ATCC824*. Gene, 1993. 123 (1): p. 93–97.
82. Pich, A., F. Narberhaus, and H. Bahl *Induction of heat shock proteins during the initiation of solvent formation in Clostridium acetobutylicum*. Appl Microbiol Biotechnol, 1990. 33: p. 697–704.
83. Ramos, J. L., E: Duque, P. Godoy, and A. Segura, *Efflux pumps involved in toluene tolerance in Pseudomonas putida DOT-TIE*: J Bacteriol, 1998. 180(13): p. 3323–3329.
84. Rogers, P., *Genetics and biochemistry of Clostridium relevant to development of fermentation processes*. Adv Appl Microbiol, 1986. 31: p. 1–60.
85. Rungeling, E., T. Laufen, and H. Bahl, *Functional characterisation of the chaperones DnaK, Dnaj, and GrpE from Clostridium acetobutylicum*. FEMS Microbiol Lett, 1999. (1): p. 119–123.
86. Sauer, U., J. D. Santangelo, A. Treuner, M. Buchholz, and P. Durre, *Sigma factor and sporulation genes in Clostridium*. FEMS Microbiol Rev, 1995. 17(3): p 331–340.
87. Schon, U. and W. Schumann, *Molecular cloning, sequencing, and transcriptional analysis of the groESL operon from Bacillus stearothermophilus*. J Bacteriol, 1993. 175(8): p. 2465–2469.
88. Schumann, W., *Regulation of the heat shock response in Esherichia coli and Bacillus, subtilis*. Journal of Bioscience, 1996. 21(2): p. 133–148.
89. Soucaille, P., G. Joliff, and G. Goma, *Butanol tolerance and autobacteriocin production by Clostridium acetobutylicum*. Current Microbiology, 1987. 14: p. 295–299.
90. Spain, J. C., *Biodegradation of nitroaromatic compounds*. Annu Rev Microbiol, 1995. 49: p. 523–555.
91. Staples, R. R., B. S. Miller, M. L. Hoover, Q. Chou, and U. N. Streips, *Initial studies on a Bacillus subtilis mutant lacking the DNAK-homologue protein*. Curr-Microbiol, 1992. 24: p. 143–149.
92. Terracciano, J. S. and E. R. Kashket, *Intracellular conditions required for the initiation of solvent production by Clostridium acetobutylicum*. Applied and Environmental Microbiology, 1986: 52: p. 8&91.
93. Tummala, S. N. E. Welker and E. T. Papoutsakis, *Development and characterization of a gene-expression reporter system for Clostridium acetobutylicum ATCC 824*: Applied and Environmental Microbiology, 1999. 65: in press (September issue).
94. van der Westhuizen, A., D. T. Jones, and D. R. Woods, *Autolytic activity and butanol tolerance of Clostridium,*

95. Vayssier, C., D. Mayrand, and D. Grenier, *Detection of stress proteins in Porphyromonas gingivalis and other oral bacteria by western immunoblotting analysis.* FEMS Microbiol Lett, 1994. 121(3): p. 303–307.
96. Volker, U., H. Mach, R. Schmid, and M. Hecker, *Stress proteins and cross-protection by heat shock and salt stress in Bacillus subtilis.* J Gen Microbiol, 1992: 138(Pt 10): p. 2125–2135.
97. Vollherbst, S. K., J. A. Sands, and B. S. Montenecourt, *Effect of butanol on lipid composition and fluidity of Clostridium acetobutylicum ATCC 824.* Applied and Environmental Microbiology, 1984. 47: p. 193–194:
98. Walter, K. A., L. D). Mermelstein, and E. T. Papoutsakis, *Host plasmid interactions in recombinant strains of Clostridium acetobutylicum ATCC 824.* FEMS Microbiology Letters, 1994. 123: p. 335–342.
99. White, D. G., J. D. Goldman, B. Demple, and S: B. Levy, *Role of the acrAB locus in organic solvent tolerance mediated by expression of marA, soxS, or robA in. Escherichia coli.* J Bacteri, 1997. 179(19): p. 6122–6126.
100. Wiesenbom, D. P., F. B. Rudolph, and E. T. Papoutsakis, *Coenzyme A transferase from Clostridium acetobutylicum ATCC 824 and its role in the uptake of acids.* Appl Environ Microbiol, 1989: 55(2): p. 323–329.
101. Wilkinson, S. R., D. I. Young, J. G. Morris, and M. Young, *Molecular genetics and the initiation of solventogenesis in Clostridium beijerinckii (formerly Clostridium acetobutylicum) NCIMB 8052.* FEMS Microbiol Rev, 1995. 17(3): p. 275–285.
102. Woods, D. R., Editor, *The Clostridia and Biotechnology.* 1993, Boston, Mass.: Butterworth-Heinemann.
103. Woods, D. R., *The genetic engineering of microbial solvent production.* Trends in Biotechnology, 1995: 13: p. 259–264.
104. Woods, D. R. and S. J. Reid, *Regulation of nitrogen metabolism, starch utilization, and the β-hbd-adhl gene cluster in Clostridium acetobutylicum.* FEMS Microbiology Reviews, 1995. 17(3): p. 299–306.
105. Wu, S. C., R. Ye, X. C. Wu, S. C. Ng, and S. L. Wong, *Enhanced secretory production of a single-chain antibody, fragment from Bacillus subtilis by-coproduction of molecular chaperones.* J Bacteriol, 1998. 180(11): p. 2830–2835.
106. Young, M., M. E. Collins, J. D. Oultram, and A. Pennock, *Genetic exchange and prospects for cloning in Clostridia, in Bacillus molecular genetics and biotechnology applications,* A. T. Ganeson and J. A. Hoch, Editors. 1986, Academic Press: Orlando. p. 259–281.
107. Yura, T. and K. Nakahigashi, *Regulation of the heat-shock response.* Curr Opin Microbiol, 1999. 2(2): p. 153–158.
108. Zuber, U. and W. Schumann, CIRCE, *a novel heat shock element involved in regulation of heat shock operon dnaK of Bacillus subtilis.* J. Bacteriol, 1994. 176(5): p. 1359–1363:
109. Nair, R., Green E., Bennett, G. N. and Papoutsakis, E. T. "Regulation of the sol locus genes for butanol and acetone production in *Clostridium acetobutylicum* ATCC 824 by a putative transcriptional repressor", *J. Bacteriol.* 181: 319–330 (1999).
110. Cornillot, E., Nair, R., Papoutsakis, E: T., & Soucaille, P. "The genes for butanol and acetone formation in *Clostridium acetobutylicum* ATCC 824 reside on a large plasmid whose loss leads to strain degeneration", *J. Bacteriol.* 179: 5442–5447 (1997).
111. Desai, R., Nielsen, L. K, and Papoutsakis, E. T. "Stoichiometric modeling of *Clostridium acetobutylicum* fermentations, with nonlinear constraints", *J. Biotechnol.* 71: 191–205 (1999).
112. Green, E. M., Boynton, Z. L., Harris, L. M., Rudolph, F. B., Papoutsakis, E. T., & Bennett, G. N., Genetic manipulation of acid formation pathways by gene inactivation in *Clostridium acetobutylicum acetobutylicum* ATCC824, *Microbiology* 142: 2079–2086 (1996):
113. Boynton, Z. I., Bennett. G. N., & Rudolph, F. B., Cloning, sequencing and expression of genes encoding phosphotransacetylase and acetate kinase from *Clostridium acetobutylicum* ATCC824. *Appl. Environ. Microbiol.* 62: 2758–2766 (1996).
114. Green, E. M., & Bennett, G. N., Genetic manipulation of acid and solvent formation in *Clostridium acetobutylicum* ATCC 824, *Biotechnol Bioeng.* 58: 215 221 (1998).
115. Desai, R., and Papoufsakis, E. T., Antisense RNA strategies for the metabolic engineering of *Clostridium acetobutylicum.* Appl. Environ. Microbiol. 65: 936–945 (1999).
116. Bermejo, L. L., Welker, N. E. and Papoutsakis, E. T., Heterologous expression of *Clostridium acetobutylicum* ATCC824 genes in *Escherichia coli* for acetone production and acetate detoxification, *Appl. Environ. Microbiol.* 64: 1079–1085 (1998).
117. Belouski, E., Watson, D. E., & Bennett, G. N., Cloning, sequence and expression of the phosphofructokinasegene of *Clostridium acetobutylicum* ATCC 824 in *Escherichia coli, Current Microbiology* 37: 17–22 (1998).
118. Belouski, E., Gui, L., Rudolph, F. B., & Bennett, G. N., Complementation of an *Escherichia coli* polypeptide deformuylase mutant with a gene from *Clostridium acetobutylicum* ATCC 824. *Current Microbiology* 36: 248–249 (1998).
119. Papoutsakis, E. T., and Bennett, G: N. "Metabolic Engineering of *Clostridium acetobutylicum*", pp. 253–279, Chapter 11 in "Metabolic Engineering" (S. Y. Lee and E. T: Papoutsakis, Eds), Marcel Dekker, 1999.
120. Lee, S. Y: and Papoutsakis, E. T., and Bennett, G. N. "The Challenges and Promise of Metabolic Engineering", pp. 1–12, Chapter 1 in "Metabolic Engineering" (S. Y. Lee and E. T. Papoutsakis, Eds), Marcel Dekker, 1999.
121. Desai, R. P., Harris, L. M., Welker, N. E., Papoutsakis, E. T. "Metabolic flux analysis elucidates the importance of the acid-formation pathway in regulating solvent production by *Clostridium acetobutylicum*", Metabolic Engineering, in press.
122. Tummala, S., Welker, N. E., and Papoutsakis E. T., Development and characterization of a gene-expression reporter system for *Clostridium acetobutylicum* ATCC 824. *Appl. Errviron. Microbiol.* 65 (In press, September 1999 issue).
123. Harris, L. M., Desai, R. P. Welker, N. E. Papoutsakis, E. T. "Characterization of recombinant strains of the *Clostridium acetobutylicum* butyrate. kinase inactivation mutant: need for new phenomenological models for solventogenesis and butanol inhibition?", *Biotechnol. Bioeng*, accepted (1999).
124. Tyurin, M., Padda, R., Huang, K. Wardwell, S., Caprette, D. & Bennett, G. N., Electrotransformation of *Clostridium acetobutylicum* ATCC824 using high-voltage radio frequency modulated square pulses, submitted.
125. Lyrists, M., Boynton, Z. L., Petersen, D. J., Kan, Z., Bennett G. N., & Rudolph, F. B., Cloning, sequencing, and characterization of the gene encoding flagellin, flaC, and the post-translational modification of the flagellin from *Clostridium acetobutylicum* ATCC 824, submitted.

126. Huang, K.-x., Rudolph, F. B., and Bennett, G: N. Characterization of methylglyoxal synthase from *Clostridium acetobutylicum* ATCC824, and its use in the formation of 1,2-propanediol. *Appl. Environ. Microbiol.* 65:3244–3247 (1999).
127. Harris, L. M. Fermentation characterization of *Clostridium acetobutylicum* ATCC 824 recombinant strains. MS Thesis, Northwestern University, December 1997.
128. Desai, R: Development of metabolic flux analysis arid antisense RNA technologies as tools for the metabolic engineering of *C. acetobutylicum* ATCC 824. PhD Thesis, Northwestern University, December 1998 . . .
129. Blank, L. Molecular and fermentatiori characterization of recombinant strains of *C. acetobutylicum* for production of chemicals, MS Thesis, Northwestern University & Dortmund University, December 1997.
130. Tummala, S. B. Development and characterization of a gene-expression reporter system for *Clostridium acetobutylicum* ATCC 824.MS Thesis, Northwestern University, June 1999.
131. Belouski, E. Cloning and sequencing of genes involved in glycolysis from, *Clostridium acetobutylicum*. MS Thesis, Rice University, May 1996.
132. Wardwell, S: A. Metabolism of acetoin in *Clostridium acetobutylicum* ATCC 824, PhD Thesis, Rice University, May 1999:

SUMMARY OF THE INVENTION

Figure 1:
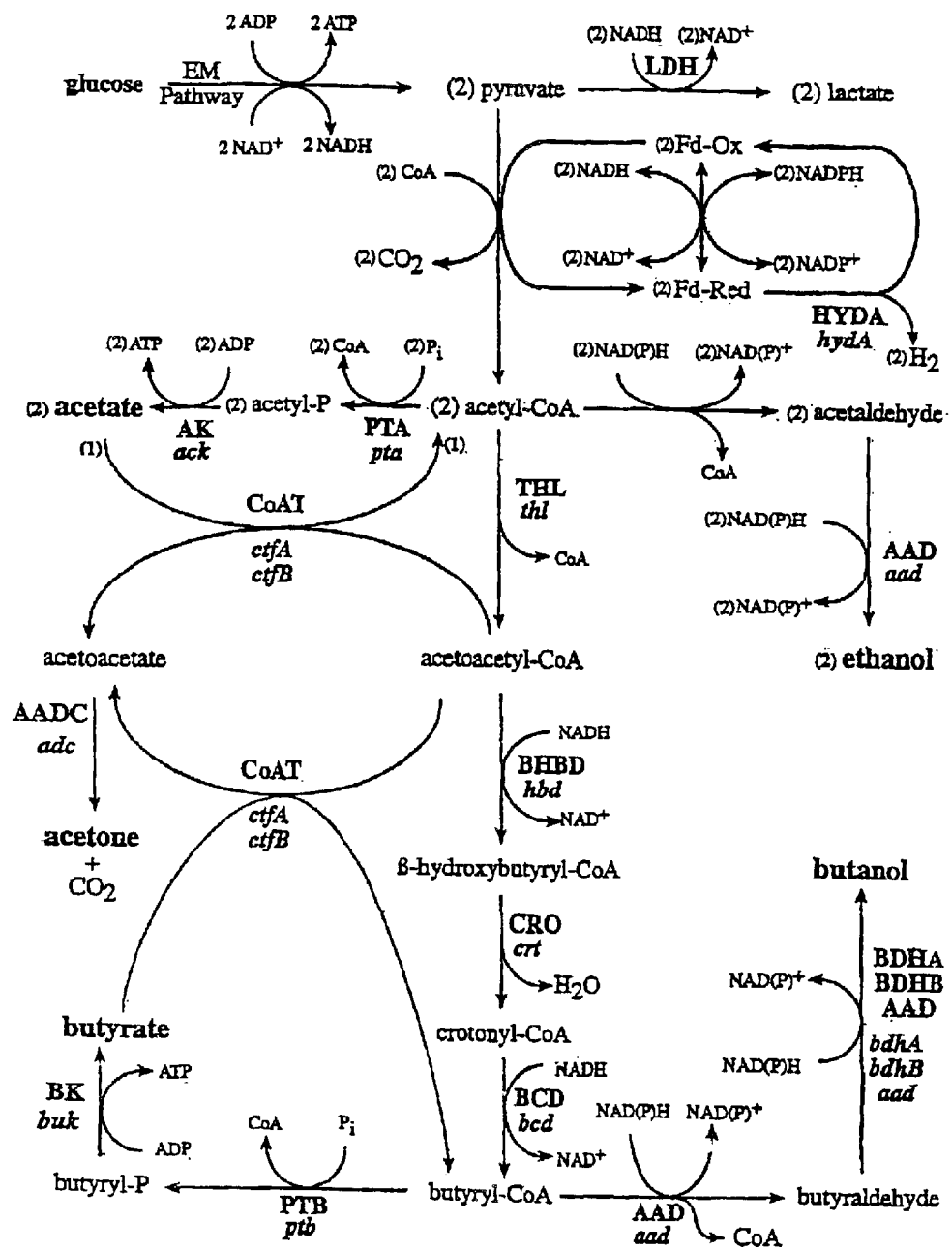
FIG. 1 provides a schematic representation (prior art) showing the major biochemical pathways for *C. acetobutylicum*. Genes that have been cloned are labeled in italics. Enzyme names indicated in bold and are abbreviated as follows: LDH, lactate dehydrogenase, HYDA, hydrogenase, PTA, phosphotransacetylase, AK, acetate kinase, THL, thiolase, CoAT, CoA transferase, AADC, acetoacetate decarboxylase, BHBD, β-hydroxybutyryl DH, CRO, crotonase, BCD, butyryl-CoA DH, PTB, phosphotransbutyrylase, BK, butyrate kinase, AAD, alcohol/aldehyde DH, and BDHA & BDHB butanol DH (isozymes A & B).
Figure 2A:
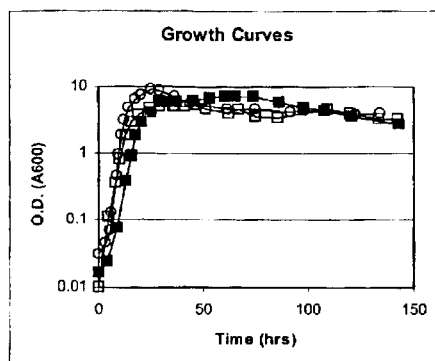
FIGS. 2A–E plot graphically, in comparison with wild and control strains, solvent/product formation as a function of time, employing a recombinant bacterium carrying a representative plasmid constructed to overexpress the groESL operon genes, in accordance with this invention. Wild type (open circles); 824(pGROE1) (closed squares); 824 (pSOS95del) (open squares).
Figure 2B:
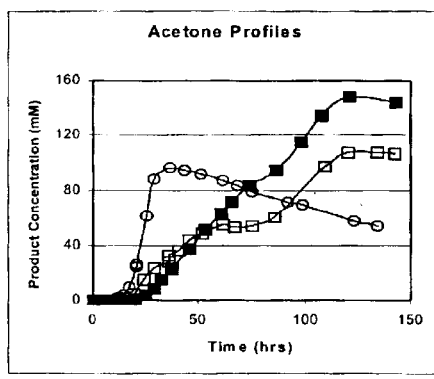
Figure 2D:
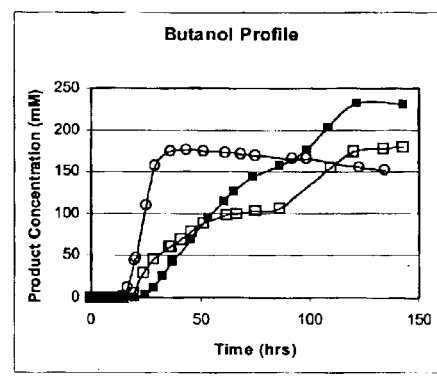
Figure 2C:
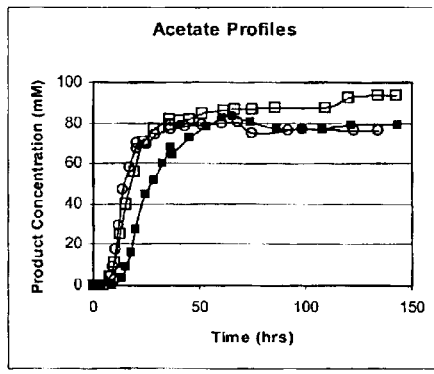
Figure 2E:
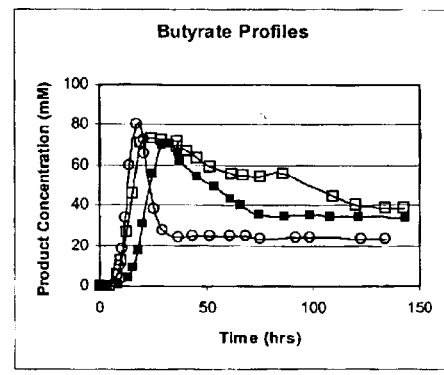

In light of the foregoing, it is an object of the present invention to provide a method of increasing cellular resistance to toxic organic molecules, thereby addressing various issues and concerns of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide an organism genetically manipulated to permit increased resistance to toxic organic molecules.

It is an object of the present invention to provide an organism genetically manipulated to either elevate expression of solvent-tolerance genes or to overexpress stress response and/or heat shock proteins to increase cellular resistance to toxic organic molecules.

It is another object of the present invention to achieve higher cell densities of bacteria capable of withstanding increased levels of toxic organic molecules.

It can also be an object of the present invention, alone or in conjunction with any other objective, to provide a method for enhanced fermentation by solventogenic bacteria.

It can also be an object of the present invention, alone or in conjunction with any other objective, to provide a method of using protein expression to increase solvent titer levels from solventogenic organisms, such protein expression as can be provided through the recombinant bacteria described herein.

Other objects, features, benefits and advantages of the present invention will be apparent from this summary and its descriptions of various preferred embodiments, and will be readily apparent to those skilled in the art having basic knowledge of gene expression, peptide structure, molecular genetics, biochemistry and other related fields. Such objects, features, benefits and advantages will be apparent from the above as taken in conjunction with the accompanying examples, data, figures and all reasonable inferences to be drawn therefrom.

In part, the present invention includes an organism, either prokaryote or eukaryote, with manipulated genetic code or material to increase cellular resistance to toxic organic molecules. In particular, a strain of bacteria may be constructed by transforming a plasmid containing genes for a stress response protein into a bacteria strain for gene expression, such bacteria as can be used for solventogenesis, bioremediation, biocatalysis, or other types of production and/or biotransformation of toxic organic molecules. It will be readily apparent to the skilled artisan that the plasmid may be either episomal or integrating. Plasmid construction and transformation may be accomplished by common methods known by those of ordinary skill in the art. The constructed plasmid contains genetic code which permits the expression of stress response proteins, such material which may include but is not limited to heat shock proteins GroES/EL or DnaK, and/or a combination of the same.

In a preferred embodiment, the constructed plasmid allows for the overexpression of such stress response proteins. This may be accomplished by methods known in the art, such as providing the genetic sequence for a stress response gene or by expressing a gene for an inducer protein for the endogenous stress response protein operon. For example, the genetic sequence of the constructed plasmid may include the groE operon of *C. acetobutylicum*. In the alternative, or in combination with the groE operon, the constructed plasmid may contain the dnaK operon, or the genetic sequence for other stress response proteins from other bacteria having similar characteristics. The operons coding for the stress response proteins may be under the control of their own natural promoters or other promoters designed to overexpress the operons. The manipulated bacteria having the constructed plasmid should then exhibit enhanced and prolonged fermentation and reduced cell lysis, both resulting in elevated levels of toxic organic molecules such as butanol compared to control or wild type strains.

In an alternative embodiment, a strain of bacteria may be designed by removing or inactivating genetic material which normally suppresses expression of solvent tolerant genes that confer increased resistance to toxic organic molecules and/or compounds. For example, the removal of a negative regulatory element such as CIRCE or the inactivation of the genes which encode repressor proteins of solvent tolerant proteins also leads to elevated expression of specific solvent-tolerance genes. Expression of such genes provides increased tolerance to solvents or other toxic organic molecules and produces increased titers of solvent during bioproduction. Examples of such solvent-tolerance genes are those which increase cellular resistance to toxic organic molecules and may also include proteins of the multi-drug efflux pump family. Regardless, whether manipulation is by downregulation, overexpression or a combination thereof, preferred recombinant species can be but are not limited to those of the genus *Escherichia*, genus *Clostridum*, genus *Lactobacilli* or genus *Bacillus*. As provided below, other such recombinant bacteria are also included, as part of this invention.

In part, the present invention also includes a method of solvent production and/or of using protein expression to enhance solvent titers by providing a cell line such as solventogenic *clostridia* and manipulating the genetic code of the cell to overexpress stress response proteins. Upon providing media and/or conditions suitable for cell growth and the production of solvent by-products from cellular metabolism, the manipulated cells demonstrate increased resistance to the solvents and thereby enhanced solvent titers are achieved. Although solventogenic *clostridia* are described herein, the methodologies of this invention can be extended to include other types of cells to produce solvents such as, but not limited to, butanol, methanol, ethanol, and acetone. The genetic manipulation of such cell lines are in accordance with the teachings herewith and will be understood by those skilled in the art. In addition, conditions suitable for cell growth and the production of useful metabolic by-products may be varied depending on the cell and the particular need for nutrients, temperature and/or oxygen, such variations also known by those skilled in the art.

In part, the present invention is also directed to one or more methods of obtaining increased solvent titer levels from solventogenic organisms. This may be accomplished by alternate, but related methods including prolonging the fermentation stage of solventogenic cells such as solventogenic *clostridia* or other anaerobic, Gram-positive bacteria. Such solventogenic cells can be introduced to a variety of culture or fermentation systems, batch or otherwise, the constitution of which will be well-known to those skilled in the art. The fermentation stage of solventogenic cells may be increased by the overexpression of heat shock proteins. As discussed above, genetic sequences encoding heat shock proteins include the groE operon and dnaK operon. The dnaK operon is made up of the genes orfA, grpE, dnaK, dnaJ, orfC, and orfD. OrfA is apparently similar to the repressor protein HrcA of CIRCE regulated heat shock genes of *B. subtilis*, and its overexpression may be undesirable. In addition, the orfC and orfD genes are of unknown function. With this, a genetic sequence constructed with the genes grpE, dnaK and dnaJ can be transformed into solventogenic cells by either a plasmid or through other methods known by those skilled in the art. These genes may be overexpressed by a promoter functional during both the exponential and stationary phases of culture. As would be apparent to one of ordinary skill the art, other genetic sequences encoding different stress response proteins may be used in combination or alone to obtain the same results, including overexpression of the groE operon (ca. 2.2 kB in size), and groE and the dnaK, dnaJ, and grpE genes of the dnaK operon (thus, total size, for all 5 genes, of ca 6 kb) simultaneously from one plasmid but with different, promoters. Overexpression of the stress response proteins provide the solventogenic cells increased tolerance to the solvent byproducts produced during fermentation. With increased tolerance, the solventogenic cells are able to produce greater yields of solvents or other products.

Alternatively, stress response proteins may also be overexpressed by suppressing the expression of the gene which codes for a putative repressor using either the gene-knockout or antisense RNA techniques. For example, the putative repressor protein orfA of *C. acetobutylicium* ATCC 824 acts through the CIRCE DNA element which is found in front of the structural genes of both the groE and dnaK operons (as also in *B. subtilis* and *E. coli*). Such a method would be also of practical significance since the increased HSP production is achieved by a single gene inactivation rather than the overexpression of several structural genes.

While several aspects of this invention have been discussed, in the preceding, with respect to certain bacteria and/or recombinant strains thereof, it will be understood by those skilled in the art made aware of this invention that such aspects can be applied more generally to a wide variety of bacteria including, but not limited to the following: solventogenic bacteria and/or related *clostridia* (e.g., *C. acetobutylicum, C. beijerickii, C. cellulolyticum, C. thermocellum, C. butyricum, C. saccharoperbutylacetonicum*, and others), *Escherichia* (including *E. coli*), *Zymomonas mobilis, Enterobacter, Serratia, Erwinia*, acetic acid bacteria, *Bacillus* (including *B. subtilis*), *Lactobacilli, Pseudomonas*, methylotrophic bacteria, *Acetobacter, Lactococcus, Arthrobacter, Ralstonia, Gluconobacter, Klebsiella, Propionibacterium, Eubacterium, Streptomyces*, and *Rhodococcus*.

Likewise, the present invention and related methodologies can be effected, as would be understood in the art, through use of all major yeast genera and/or recombinant strains thereof, including, but not limited to, the following: *Saccharomyces, Schizosaccharomyces, Kluyveromyces, Candida, Pichia* and methylotropic yeast. Alternatively, and without limitation, various filamentous fungi and/or recombinant strains thereof can be employed: *Aspergillus, Trichoderma, Rhizopus, Microsponon, Fusarium, Neurospora* and *Penicillium*, using techniques described herein or straightforward modifications thereof, as would be understood by those skilled in the art made aware of this invention.

More generally, the present invention can relate to one or more methods of using a heat shock protein or the expression thereof to increase microorganism tolerance to a toxic substance. Such a method includes (i) providing a recombinant microorganism transformed by a plasmid comprising genetic code to increase expression of a heat shock protein; (ii) providing an appropriate fermentation system; and (iii) contacting the recombinant microorganism with the system over a time sufficient for expression of the heat shock protein. Microorganisms useful for such a method include, but are not limited to those provided above, depending upon a particular system and desired fermentation effect. For instance, various solventogenic bacteria can be utilized where the toxic substance may be the solvent or a solvent by-product of such a system, such toxins/products/solvents including, but not limited to, butanol, acetone, ethanol and other substances of the sort described herein.

Various other microorganisms and/or recombinant strains thereof can include, but are not limited to, those provided above, depending upon a particular bioremediation system, in which this invention can be used to increase/enhance tolerance of a toxic substance such as, but not limited to, a wide variety of organic compositions (e.g., alcohols, carboxylic acids, ketones, aldehydes, hydrocarbons and derivatives, derivatives of carboxylic acids, ethers, amines, phenols, glycols, epoxides, keto acids, hydroxy acids, heterocyclic compounds, others), but also organometallic compounds and inorganic toxic substances that can be metabolized by organisms. Of the available recombinant microorganisms, a species from the genus *Aspergillus* is preferred, although other bacteria, yeast or fungi could be used as described herein. In a similar fashion, such microorganisms or recombinant variations thereof can be employed as part of a biocatalytic system, wherein expression of a heat shock protein increases tolerance to the starting substrate material, byproduct, the resulting product or a combination of the three. With reference to the preceding biomediation discussion, such substrates and/or products can include those listed therewith, the identity of which will determine the microorganism employed. In light of such considerations, preferred recombinant microorganisms include but are not limited to species from the genus *Escherichia*, genus *Saccharomyces* and genus *Pichia*, each of which can be provided as described herein and/or through recombinant techniques well known to those skilled in the art.

Preferred embodiments of this invention have been described using a plasmid in conjunction with the recombinant techniques. However, as would be understood by those skilled in the art, bacteriophage can be used as cloning vectors. The feasibility of phage-cloning vectors in *C. acetobutylicum* was discussed in the prior art in a non-related context. See, Jones and Woods, "Acetone-Butanol Fermentation Revisited," Microbiological Reviews, 1986, 50: 484–524. Accordingly, the present invention also contemplates use of a bacteriophage appropriate for increased expression of a heat shock protein, in conjunction with the methodologies and/or recombinant microorganisms described herein.

While various examples, tables, figures and supporting data are provided, for purposes of general illustration, in the context of solvent production and increased tolerance thereto, it will be understood by those skilled in the art that the present invention can be readily extended to a variety of bioremediation and biocatalytic systems. For instance, the availability of microorganisms to perform bioremediation and/or biocatalysis has been, in both instances, shown to be limited by the toxic effects of the substrate, target molecule, product and/or byproduct—in a manner analogous to that described herein for solvent production. With regard to biocatalysis and the effect of such toxins on microorganisms, consider, for example, "Production and Biotransformation of 6-pentyl-alpha-pyrone by *Trichoderma harzianum* in Two-phase Culture Systems," Serrano-Carreon L, Balderas-Ruiz K, Galindo E, Rito-Palomares M Applied Microbiology and Biotechnology 58 (2): 170–174 February 2002; and "Organic Solvent Toxicity in Photoautotrophic Unicellular Microorganisms," Leon R, Garbayo I, Hernandez R, Vigara J, Vilchez C Enzyme and Microbial Technology 29(2–3): 173–180 Aug. 72001. With regard to bioremediation and resulting toxicity, among other references, see "Detoxification of Reactive Intermediates During Microbial Metabolism of Halogenated Compounds," Vlieg JETV, Poelarends G J, Mars A E, Janssen D B Current Opinion in Microbiology 3 (3): 257–262 June 2000; and "In situ Bioremediation through Mulching of Soil Polluted by a Copper-Nickel Smelter," Kiikkila O, Perkiomaki J, Barnette M, Derome J, Pennanen T, Tulisalo E, Fritze H Journal of Environmental Quality 30 (4): 1134–1143 July–August 2001. While the prior art acknowledges such concerns, no solution is forthcoming.

Accordingly, it will be understood that the effectiveness of a bioremediation or biocatalytic process can be enhanced by increased tolerance to a corresponding toxic substance—through a straightforward extension of the methodologies and recombinant microorganisms of this invention. Whereby overexpression of heat shock proteins are shown herein to increase solvent production, such expression can also be used to mitigate various other toxic effects. As a result, use of the present invention can provide for bioremediation or biocatalysis under conditions which might otherwise preclude such processes.

Illustrating the design and development of several preferred embodiments of this invention it is first important to more completely understand two common stress response proteins useful for the above-identified methods and constructs. GroESL and DnaKJ are two stress response proteins of the type commonly referred to as heat shock proteins. The two corresponding operons were cloned from *C. acetobutylicum*. The groE operon consists of two genes, groES and groEL. The dnaK operon consists of seven genes, orfA, grpE, dnaK, dnaJ, orfB, orfC, and orfD. The groE operon is transcribed as a bicistronic message that is 2.2 kb in length with a transcription terminator site downstream of groEL and a transcriptional start site located upstream of groES. Two transcription start sites were identified for dnaK operon. One transcriptional start site was located upstream of orfA, while the other is upstream of grpE. The sizes of the four different transcripts were 5.0, 3.8, 3.8, and 2.6 kb, respectively. Putative ribosome-binding sites for both the groE and dnaK operons showed homology to the ones in *E. coli*, and to those of gram-positive bacteria. Putative promoter sequences were also determined and were shown to bear homology with consensus promoter sequences of gram-positive bacteria. Recently, the DnaK, DnaJ, GrpE, and OrfA of *C. acetobutylicum* were shown to refold guanidium hydrochloride-denatured firefly luciferase in vitro. Furthermore, the DnaK system from *C. acetobutylicum* was also shown to prevent the aggregation of OrfA from *C. acetobutylicum*. orfA codes for a putative repressor of the dnaK operon through a CIRCE regulatory element similar to the one in *B. subtilis*.

The bacteria *C. acetobutylicum* ATCC 824 has been used to illustrate this invention because all of the genes shown on FIG. 1 have been cloned and its physiology is by far the most widely studied among *C. acetobutylicum* strains. The US DOE has gone as far as publishing the physical and genetic map of this organism. Although solventogenic *clostridia* such as *C. acetobutylicum* ATCC 824 has been tested as more fully described below, it should be apparent that these same principles apply more broadly to other anaerobic prokaryotes, both for producing solvents like butanol and acetone, or for producing other chemicals and enzymes for biotransformations and applications in bioremediation.

Further, research with other microorganisms has shown that proteins of the multi-drug efflux family play a role in solvent tolerance. Multi-drug efflux pumps serve to detoxify the intracellular environment via the export of toxic organic components. In *E. coli*, the acrAB operon forms a multi-drug efflux pump that has been found to be highly expressed in solvent tolerant mutants. In addition, deletion of acrAB has been found to result in loss of tolerance to both n-hexane and cyclohexane. Expression of acrAB and other related genes are modulated by the transcriptional regulators encoded by marR, marA, soxR, and soxS. In fact, overexpression of marA and soxS was found to elevate organic solvent tolerance of several *E. coli* strains. In *B. subtilis*, two multi-drug efflux proteins have been found to confer resistance to various organic compounds (ethidium bromide, acridine dyes, fluoroquinolone antibiotics, etc.). blt and bmr are genes coding for these highly homologous transporters whose expression is controlled by the regulators encoded by bltR and bmrR respectively. In *Pseudomonas aeruginosa*, antibiotic resistance and solvent tolerance has been linked to the action of several efflux pumps: MexA-MexB-OprM, MexC-MexD-OprJ, and MexE-MexF-OprN. These pumps are comprised of a periplasmic linker protein (MexA, MexC, and MexE), a cytoplasmic protein (MexB, MexD, and MexF), and an outer membrane protein (OprM, OprJ, and OprN). Similar efflux systems have been found in *P. putida* strains and were shown to impact solvent tolerance. Several of these genes are collectively shown in Table 1 below. The same methodologies and constructs discussed herein may be used to develop solvent resistant strains of bacteria by the overexpression of these same or similar proteins.

related methods provide results and data which are surprising, unexpected, and contrary to the prior art. While the utility of this invention is illustrated through the use of several constructs and methods which can be used therewith, it will be understood by those skilled in the art that comparable results are obtainable with various other constructs and/or methods, as are commensurate with the scope of this invention.

General Methods.

Stoichiometric Flux Analysis Using a Physiological Constraint.

The underlying assumption that product yields are only affected by the enzymes involved in the final steps of product synthesis may be too simplistic. Significant enhancement of product yields may only be realized by taking a more global approach to quantitatively understanding cellular metabolism. A most useful approach, metabolic flux analysis (MFA), using metabolic pathway balances to develop a model of cellular metabolism was proposed by Papoutsakis in 1984. This model takes the form of a system of linear equations based on species balances and in vivo metabolic pathway fluxes. The system of equations is typically underdetermined and must be further manipulated to be useful, typically using biological constraints in the form of pseudo-steady state approximations on metabolic intermediates. However, the presence of an unresolved singularity has prevented the calculation of some pathway fluxes critical in the metabolism of *C. acetobutylicum*. Thus, a

TABLE 1

Organic solvent tolerance homologs in the *C. acetobutylicum* ATCC824 gnome

| Organism & Gene | Protein Size (aa) | Function/Role of Protein | *C. acetobutylicum* ATCC824 Homolog Percent Identity (Similarity) & Position |
| --- | --- | --- | --- |
| *E. Coli* acrB | 1049 | Transmembrane component of a major efflux pump | 23% (44%) over 782 aa @ 89613–91907 |
| *E. Coli* acrR | 215 | Regulator of acrAB operon | 25% (54%) over 159 aa @ 3525884–3526357 |
| *E. Coli* marA | 129 | Transcriptional activator of the mar (multiple antibiotic resistance) operon (responsible for environmental stress factors) | 30% (60%) over 98 aa @ 152061–152354 |
|  |  |  | 30% (58%) over 97 aa @ 1131958–1132245 |
|  |  |  | 29% (54%) over 91 aa @ 1258122–1257850 |
|  |  |  | 28% (51%) over 97 aa @ 2605268–2604981 |
|  |  |  | 28% (43%) over 99 aa @ 3235580–3235287 |
| *E. Coli* soxR | 125 | Repressor of the mar operon | 27% (47%) over 106 aa @ 3166960–31667274 |
|  |  |  | 25% (46%) over 96 aa @ 664993–665280 |
| *E. Coli* soxR | 154 | Transcriptional activator of the AraC subfamily | 30% (46%) over 95 aa 3269119–3269403 |
|  |  |  | 24% (52%) over 113 aa @ 664993–665280 |
| *E. Coli* soxS | 107 | Transcriptional activator of the AraC subfamily | 31% (62%) over 98 aa @ 152061–152354 |
|  |  |  | 31% (55%) over 91 aa @ 1258122–1257850 |
|  |  |  | 27% (56%) over 103 aa @ 2605286–2604981 |
| *B. subtilis* bltR | 273 | Regulator of blt expression | 28% (53%) over 268 aa @ 3306158–3306973 |
| *B. subtilis* blt | 400 | Multi-drug efflux protein | 24% (44%) over 379 aa @ 543493–542330 |
| *B. subtilis* bmr | 389 | Multi-drug efflux protein | 19% (39%) over 353 aa @ 543430–542330 |
| *B. subtilis* bmR | 279 | Regulator of bmr expression | 25% (45%) over 275 aa @ 3306164–3306970 |
| *P. aeruginosa* MexB | 1046 | Cytoplasmic component of multi-drug efflux pump | 25% (46%) over 765 aa @ 89730–91973 |
| *P. aeruginosa* MexD | 1043 | Cytoplasmic component of multi-drug efflux pump | 22% (45%) over 692 aa @ 89931–91973 |
| *P. aeruginosa* MexF | 1062 | Cytoplasmic component of multi-drug efflux pump | 20% (40%) over 781 aa 89724–91988 |

EXAMPLES OF THE INVENTION

The following non-limiting examples and data illustrate various aspects and features relating to the constructs and/or related methods of the present invention, including organisms and/or the development of cells resistant to toxic organic compounds and achieving increased solvent titers, as are available through the methodologies described herein. In comparison with the prior art, the present constructs and novel technique has been developed using a physiological nonlinear constraint relating the fluxes around the singularity through a software code utilizing a model independent heuristic global optimization approach to solve the resultant nonlinear problem. The use of the nonlinear constraint has been validated by correlating calculated butyrate production pathway flux profiles with measured intracellular pH profiles. This model was used to analyze fermentation data from several *C. acetobutylicum* strains. Flux analysis revealed previously obscured roles for the acid formation pathways. The acetate formation pathway supported significant fluxes throughout the stationary phase while the butyrate formation pathway was found to uptake butyrate.

Antisense RNA (asRNA) as a Metabolic Engineering Tool.

AsRNA strategies may offer a number of advantages over gene inactivation for metabolic engineering, such as rapid implementation, and the ability to inducibly repress protein production using inducible promoters. For example, asRNA has been implicated in the regulatory mechanisms of a number of genes, most notably the glutamine synthetase of a *Clostridium* species. Strain 824(pRD4) was developed to putatively produce a 102 nucleotide asRNA with 87% complementarity to the buk gene and exhibited 85%–90% lower BK and AK specific activities and 45%–50% lower PTB and PTA specific activities. Strain 824(pRD4) also exhibited earlier induction of solventogenesis resulting in 50% and 35% higher final titers of acetone and butanol, respectively. Strain 824(pRD1) was developed to putatively produce a 698 nucleotide asRNA with 96% complementarity to the ptb gene, and exhibited 700/o and 80% lower PTB and BK activities respectively. Strain 824(pRD1) also exhibited 300% higher levels of a lactate dehydrogenase. While levels of acids were unaffected in 824(pRD1) fermentations, acetone and butanol titers were reduced by 96% and 75%, respectively. This reduction in solvent production by 824 (pRD1) was compensated by ~100 fold higher levels of lactate production. The lack of significant impact on butyrate formation fluxes by reduced PTB and BK enzyme levels suggests that butyrate formation fluxes are not controlled by the levels of the butyrate formation enzymes. Such strategies and related technologies can, of course, be applied to methods for downregulation of genes that interfere with the expression of heat shock proteins in microorganisms.

Phenomenological Regulation of Solvent Formation.

In batch fermentation, the growth phase of solventogenic *clostridia* is acidogenic, i.e., producing acetate, butyrate and $H_2$ to meet cellular needs for ATP (FIG. 1). In the non-growth associated solventogenic phase, acetone and alcohol formations are accompanied by reduced $H_2$ production and, frequently, uptake of butyrate and acetate. Several fermentation conditions have been found to effect product formation and the initiation of solvent formation, and include the beneficial effects of low pH, carboxylic-acid additions, phosphate, iron, and nitrogen limitations, and inhibitors (such as CO) of $H_2$ formation. Some of the conditions that bring about the metabolic switch involved in solventogenesis were also found to induce the stress (heat shock) response.

Transformation, Vectors & Host-Plasmid Interactions.

Electrotransformation has become the method of choice for introducing DNA. In the present invention, a restriction system (Cac824I) in strain ATCC 824 has been identified which frequently cuts DNA originating from *E. coli* or other G+C rich DNA and prevents efficient transformation. An in vivo system has been developed for methylating DNA (in *E. coli*) specifically at Cac824I recognition sites thereby protecting it from restriction. Several *E. coli-C. acetobutylicum* shuttle vectors, with various origins of replication and promoters have been reported. They have copy numbers of 7 to 14 per cell, which appears suitable for ME applications, and are segregationally quite stable. Various vectors elicit unique and unusual (but beneficial for solvent production) host-plasmid interaction effects.

Confirmation and Quantitation of Successful Transformation.

Expression (mRNA and protein) of the groE & dnaK operon genes by recombinant 824 strains constructed in the present invention must be confirmed in order to correlate enhanced butanol production with increased levels of these HSPs. In addition, strain 824 and the controls for plasmid-carrying strains, 824(pIMP1) and 824(pSOS95del) will also contain levels of the GroESL & DnaKJ proteins, but the levels may be very different between these strains. The concentration of dnaK, dnaJ, grpE, groEL, and groES mRNA can be determined by Northern blot, RT-PCR or microarray analyses.

Further, the amount of groE and dnaK operon proteins can be measured by quantitative Western blot (immunoblot) analysis experiments. These experiments will require polyclonal (or monoclonal) antibodies for these proteins. It has been found that polyclonals used with the corresponding *E. coli* proteins cross-react with the *C. acetobutylicum* proteins, believed to be a result of the fact that homologous HSP proteins in the two organisms share very high identity. Polyclonal and/or monoclonal antibodies for all major *E. coli* HSPs (as well as pure proteins) are commercially available by StressGen Biotechnologies, Victoria, BC, Canada. With an interest in relative amounts of proteins, protein quantitation through Western analysis can be thus carried out using the commercially available *E. coli* HSP proteins.

Example 1

The following illustrates a representative construction of a cell, in accordance with this invention, having increased resistance to toxic organic molecules, namely butanol. A plasmid (pSR1) is constructed using common methods known by those skilled in the art containing the groE operon of *C. acetobutylicum* under the control of its own natural promoter. pSR1 was electrotransformed into strain ATCC 824. After verifying plasmid integrity in this strain, a series of fermentations with strain 824(pSR1) and its respective control strain 824(pIMP1) were carried out. Plasmid pIMP1, a plasmid naturally occurring in *C. acetobutylicum* ATCC 824, is the backbone plasmid into which the groE operon was inserted. Strain 824(pSR1) exhibited a prolonged solvent formation stage, reduced cell lysis and reached a butanol titer of 227 mM (16.8 g/l) against a titer of 175 mM (13 g/l) for the control strain 824(pIMP1).

Example 2

The following illustrates another aspect of this invention, the elevated expression of solvent tolerant genes to increase cell resistance to toxic organic compounds. A gene (solR), identified upstream of aad was found to encode a repressor of the sol locus (aad, ctfA, ctfB, and adc) genes (located on the large pSOL1 plasmid) for butanol and acetone formation in strain ATCC 824. Overexpression of solR in 824 (pCO1) resulted in a solvent-negative phenotype due to its deleterious effect on the transcription of the sol locus genes. Inactivation of solR via homologous recombination yielded strains B and H, which exhibited deregulated solvent production characterized by increased yields and fluxes towards butanol and acetone formation, earlier induction of aad, and lower overall acid production as compared to the wild-type strain. Strains B and H were characterized by Southern and PCR analysis to confirm the recombination events and in controlled pH fermentations for product formation and flux analysis. Strain B exhibited a 32-fold and 2.1-fold increase in the final butanol and acetone concentrations, respectively compared to the wild-type. Similarly high butanol levels were exhibited by strain H. Final solvent titer increases were even higher in the strain with solR inactivation as well as overexpression of plasmid encoded aad. In total, 255 mM of butanol, 162 mM of acetone, and 43 mM of ethanol were produced by strain H(pTAAD). At 30 g/L of solvents, these are believed to be the highest solvent levels ever reported in a clostridial fermentation. Equally interesting and quite unexpectedly, this strain exceeded the level of ca 180 mM butanol which has been viewed as the upper toxicity level for this solvent.

The procedures, data and results of examples 3–10 demonstrate various methodologies of this invention, as can be affected through use of the groESL operon as representative of genetic materials and plasmids constructed therefrom, such materials and plasmids as can be used in recombinant microoogranisms for application to a number of other solvent production, bioremediation or biocatalytic systems.

Example 3a

GroESL Overexpressing Strain

A recombinant C. acetobutylicum strain carrying a plasmid constructed to overexpress the groESL operon genes (groES and groEL) under control of the clostridial thiolase promoter was created. The groESL operon genes were PCR amplified from the chromosome using primers designed to exclude the operons natural promoter and associated regulatory element. (The regulatory element, termed CIRCE (Controlling Inverted Repeat of Chaperone Expression), controls expression of the groESL operon through interaction with a putative regulatory protein orfA. OrfA is the first gene in the dnaKJ operon, the other major member of the chaperone familiy. The CIRCE element was omitted to liberate expression of the groES and groEL genes on the plasmid from control of the orfA protein produced from the chromosomal copy of the orfA gene.) The groESL operon genes were inserted into the C. acetobutylicum/E. coli shuttle vector pSOS95del. The shuttle vector was created by removing the clostridial acetone operon (ace) genes from pSOS95 (unpublished results), leaving the thiolase promoter for use in expression of cloned genes. The resulting groESL overexpression plasmid, pGROE1, was transformed into C. acetobutylicum ATCC 824 and used in subsequent characterization experiments.

Example 3b

Description of E. Coli Transformation Used in Construction of GroESL and DnaKJ Plasmids Construction of plasmids for use in C. acetobutylicum is routinely carried out in E. coli due to the ease of DNA manipulation in E. coli and the difficulties in DNA manipulation in C. acetobutylicum. Plasmids created in E. coli can then be transformed into C. acetobutylicum by electrotransformation. Initial efforts to identify an E. coli clone in which the GroESL and DnaKJ genes were successfully inserted into the shuttle vector failed to produce a positive clone. It has been shown that excessive overproduction of heat shock proteins is toxic in a number of hosts (including E. coli and B. subtilis). It was hypothesized that transformation and growth of E. coli at a lower temperature (25° C.) may lessen the impact of increased heat shock protein production. This hypothesis proved to be correct in so far as use of ambient/room temperatures resulted in the identification of positive clones. It was subsequently shown that positive clones grew up to 1000 times better at 25° C. versus cells grown at 37° C., as determined by CFU/ml counts.

Example 4

Fermentations with 824(pGROE1) and 824 (pSOS95del)

Construction of Shuttle Vector pSOS95del. Plasmid pSOS95 (available per S. B. Tummala and E. T. Papoutsakis, 1999. Development and characterization of a ene expression reporter system for Clostridium acetobutylicum ATCC 824. Appl. Environ. Microbiol. 65:3793–3799) was digested with EheI, purified with GFX DNA Purification column, and subsequently digested with BamHI. The large fragment (5.0 kb) was isolated with a GFX Gel Band Purification column and blunt-ended using Klenow fragment, Re-ligation of the large fragment resulted in the formation of the pSOS95del shuttle vector.

A series of duplicate fermentations with the 824 (pGROE1), 824(pSOS95del) control strain, and wild type 824, were carried out to examine the effects of groES and groEL overexpression on solvent formation, metabolic fluxes, and on transcriptional and protein expression patterns. In addition, the effects of the host-plasmid effect (wild type versus plasmid control) were examined. The fermenters were kept anaerobic with nitrogen and a low end pH value of 5.0 was maintained with ammonium hydroxide. Glucose was fed once during the fermentation to prevent complete depletion of glucose. Supernatants were collected for product formation analysis by HPLC, cell pellets were harvested for use in Western Blot analysis, and RNA samples were taken for use in microarray and RT-PCR analysis.

Example 5

Product Formation and Metabolic Fluxes

The presence of the pGROE1 plasmid had dramatic effects on solvent/product formation, particularly in the formation of acetone and butanol, when compared to both the wild type and control strains (Table 2, FIG. 2). The 824(pGROE1) strain produced 148 mM and 231 mM of acetone and butanol, respectively, compared to 107 mM and 178 mM in the control strain and 96 mM and 175 mM in wild type. This represents an increase in final acetone and butanol titers of 66% and 56%, respectively, relative to the 824(pSOS95del) control strain. It is also interesting to note that the onset of solvent production is delayed and appears to occur in two distinct phases for both recombinant strains. This is likely due to a frequently observed host-plasmid interaction. Final ethanol titers were slightly lower in the 824(pSOS95del) and 824(pGROE1) strains (23 mM and 21 mM, respectively) compared to the wild type 824 strain (28 mM). Acetate levels showed no statistical difference between strains, while butyrate levels were slightly lower in the two recombinant strains (73 mM and 70 mM) compared to the wild type (80 mM). The 824(pGROE1) strain grew to higher optical densities than the 824(pSOS95del) control strain, but was slightly lower than the wild type strain. The doubling time for the two recombinant strains were nearly identical (2.01 and 1.99 hours), both exhibiting slower exponential growth than the wild type (1.24 hours).

TABLE 2

Product Concentrations

| | Wild Type 824 | 824 (pSOS95del) | 824 (pGROE1) |
|---|---|---|---|
| Acetone, mM (±3) | 96 | 107 | 148 |
| Butanol, mM (±2) | 175 | 178 | 231 |
| Ethanol, mM (±1) | 28 | 23 | 21 |
| Acetate, mM (±7) | 80 | 93 | 83 |
| Butyrate, mM (±3) | 80 | 73 | 70 |
| Acetoin, mM (±1.1) | 11.6 | 5.2 | 7.8 |
| Max. O.D. (A600) | 8.88 | 5.38 | 7.18 |
| Doubling time, (hrs) | 1.24 | 2.01 | 1.99 |

(±S.D)

Example 6

Figure 3:
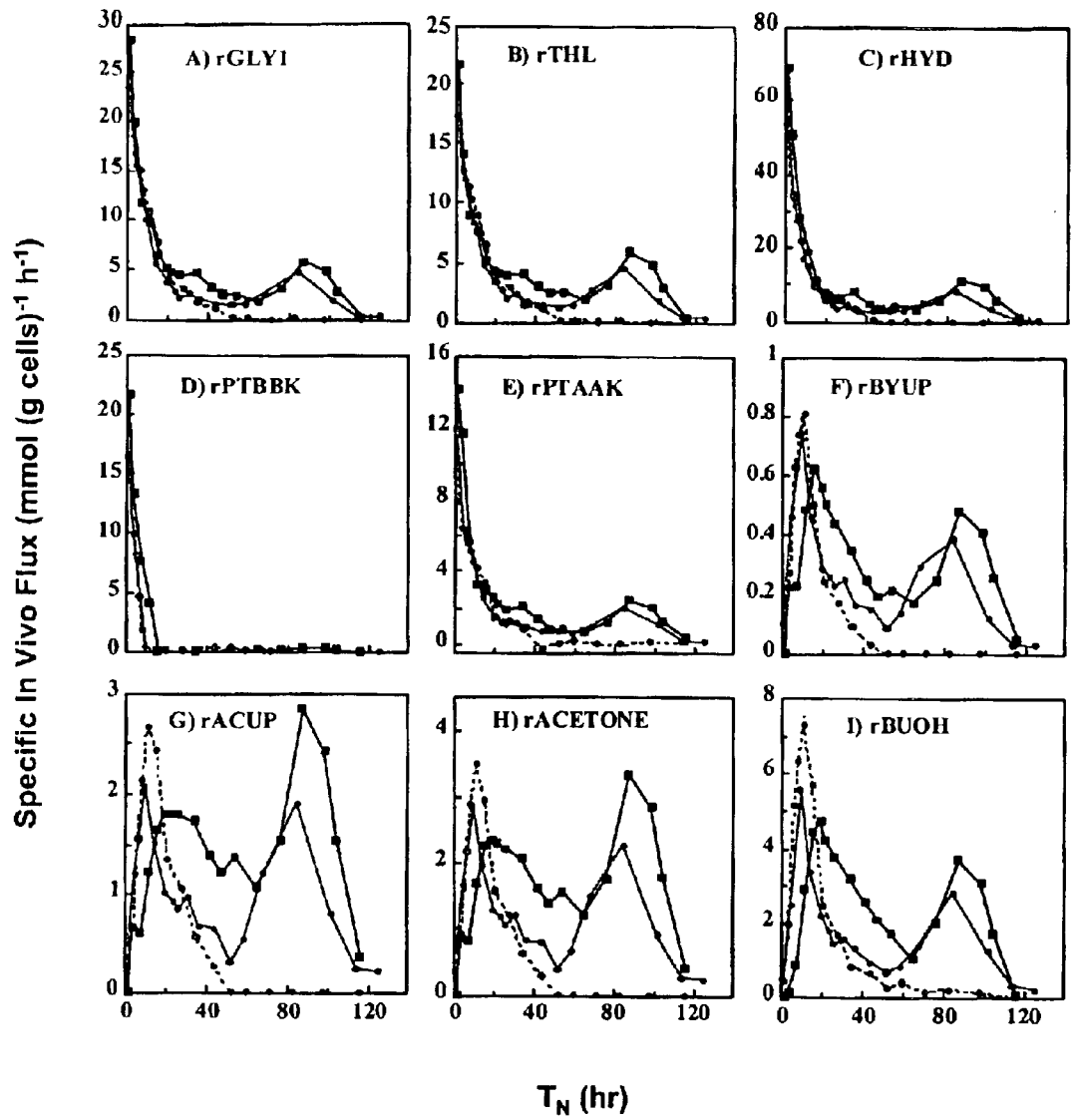
FIG. 3 provides comparative time course profiles of specific in vivo fluxes for stains 824(pGROE1) (solid squares), 824(pSOS95del) (solid circles), and wild type 824 (open circles). Data is average of two fermentations. rGLY1, glucose utilization; rTHL, acetyl-CoA utilization; rHYD, hydrogen formation; rPTBBK, butyrate formation; rPTAAK, acetate formation; rBYUP, butyrate uptake; rACUP, acetate uptake; rACETONE, acetone formation; rBUOH, butanol formation.

An examination of specific in vivo fluxes for a number of key metabolic reactions provides an excellent portrait of differences in carbon flows between various strains, while accounting for differences in cell densities. A metabolic flux analysis program, CompFlux (based on Desai et al, 1999), was utilized to calculate the metabolic in vivo fluxes for the wild type and recombinant strains. FIG. 3 shows time course profiles for nine key fluxes. The specific in vivo fluxes show drastic differences between the wild type 824, 824 (pSOS95del), and 824(pGROE1) strains. As previously mentioned, both recombinant strains exhibit two distinct phases, while the wild type exhibits only one. This pattern has been observed for other plasmid carrying strains as well, and appears to be a generalized plasmid effect. Strain 824(pGROE1) exhibited an elevated glucose utilization (rGLY1) and acetyl-CoA utilization (rTHL) relative to the control strain. The acetate and butyrate uptake rates were also higher in strain 824(pGROE1), which results in an increased acetone formation (rACETONE). Acetone, as it appears, can be formed through the uptake of either acetate or butyrate. For strain 824(pGROE1), acetate uptake (rACUP) appears to play a larger role in increased acetone production than butyrate uptake. The increases in both butyrate uptake (rBYUP) and butyrate formation (rPTBBK) are relatively small when compared to the increases in acetate uptake and acetate formation (rPTAAK). Strain 824(pGROE1) also exhibited butanol (rBUOH) formation fluxes that were significantly higher than in strain 824 (pSOS95del). The differences observed in the in vivo fluxes are in agreement with the observation of higher final solvent titers in strain 824(pGROE1), and further illustrate the delay in solvent production in both recombinant strains.

Example 7a

Microarray Analysis

Large scale transcriptional analysis has emerged as an important tool to help better understand the differences in the global genetic programming of various cell types and growth conditions. DNA microarrys with spots representing more than 1000 genes, approximately one fourth of the *C. acetobutylicum* genome, have been printed using the TIGR protocol (Hegde et al, 2000). In brief, PCR primers were designed to amplify gene fragments with an average size of 500 bp such that non-specific hybridization is minimized. The resulting PCR products were dried, redissolved in a water-DMSO solution, and spotted in triplicate on Corning CMT-GAPS™ glass microarray slides with a BioRobotics DNA arrayer. Spotting in triplicate provides for much more rigorous statistical analysis of microarray data. The slides are hybridized overnight with cDNA that has been fluorescently labeled with Cy-3 and Cy-5 and then scanned with a GSI Lumonics ScanArray analyzer. Spot intensities are quantitated with Quantarray Microarray analysis software. The data is normalized and genes which show significant expression differences are determined with a novel normalization and filtering method (currently unpublished method). In the context of the present invention, the effects of chaperonin (GroESL) overexpression, as well as the effects of other common stresses such as heat, oxygen, and solvents, are investigated.

Example 7b

Gene Clustering and Self Organizing Map (SOM) Analysis

Microarray analysis produces a large amount of data. Analyzing the data to understand the patterns of gene expression is made difficult by the fact that no two genes are likely to exhibit precisely the same response, and the behaviors present can vary tremendously. There are a number of mathematical techniques which have been previously developed which can be used to identify patterns of gene expression. Perhaps the most common method to this point has been hierarchical clustering, whereby data points are forced into a strict hierarchy of nested subsets. While useful, hierarchical clustering has shortcomings: hierarchical clustering is 1) better suited for data which is of a true hierarchical nature, such as the evolution of species, 2) suffers from a lack of robustness, nonuniqueness, and inversion problems, 3) deterministic, resulting in clustering based on local decisions without the ability to reevaluate the clustering. An alternative method, Self Organizing Maps (SOMs), are better suited to clustering and analysis of gene expression patterns. SOMs have proven themselves as significantly more robust and accurate than hierarchical clustering and are easy to implement, reasonably fast, and scalable to large data sets.

Example 8

SOM analysis was performed on the three sets of data from the experiements described above [WT824 v. 824 (pSOS95del); 824(pSOS95del) v. 824(pGROE1); and WT824 v. 824Butanol] using GENECLUSTER (Tamayo et al, 1999). Only genes which were overexpressed at one or more time points at the 95% confidence level were included in the cluster analysis. The number of clusters was determined by decreasing the number of clusters until all the clusters were unique and had no overlap in patterns. Samples from the WT824, 824(pSOS95del) and 824(pGROE1) fermentations labeled A, B, C, and D represent samples taken throughout the exponential growth phase at optical densities (A600) of 0.40, 0.88, 1.83, and 3.01 (S.D.=0.06), respectively. To date, isolation of intact RNA at later time points has not been possible due to apparent RNA instability in the stationary phase.

Example 9

Transcriptional Analysis of GroESL Overexpression

Overexpression of the GroESL operon genes appears to result in a dramatic shift in transcriptional programming when compared to the plasmid control strain. SOM analysis resulted in the identification of 3 gene clusters. Each cluster represent a set of genes which have elevated expression in the 824(pGROE1) culture at one of the three time points (B,C,D; time point A has yet to be hybridized/analyzed). Examination of the genes belonging to each cluster provides the following. First, a number of sporulation genes (primarily spoIII and spoV family genes) show an early, increased expression level in the 824(pGROE1) strain. Sporulation in wild type *Clostridium acetobutylicum* is specific to the transition to the stationary phase, and is accompanied by a shift to solvent formation, granulose accumulation, and the expression of heat shock proteins. (The extent to which these processes share common control mechanisms is largely unknown. It may be possible that overexpression of the heat shock proteins groES and groEL is involved in the regulation, either directly or indirectly, of some of the key sporulation genes. It is also possible that overexpression of the groES and groEL genes represents a stress in addition to the presence of a plasmid. Stresses in general are thought to induce sporulation.) Second, a number of chemotaxis (Che) genes are upregulated at each of the three time points. Third, there is early and enhanced expression of the flagellar genes, primarily at time point C (mid-late exponential). Increased expression of these latter two sets of genes is somewhat unexpected. Many of the sporulation genes which show increased expression in the GroESL overexpressing strain have been show to be up regulated by Spo0A. Spo0A levels were 1.1–1.4 times higher in the GroESL overexpressing strain (while these expression levels were not high enough to be included in the cluster analysis, the nine spots on the DNA-array slides representing Spo0A had an intensity correlation (Cy3 vs. Cy5) value of 0.93). However, Spo0A has also been shown to down regulate many of the chemotaxis and flaggelar genes listed above (Fawcett et al, 2000). The presence of two distinct cell populations may explain the two distinct phases of growth observed over the course of a fermentation (see FIG. 1) for this and other plasmid carrying strains (see "Transcriptional analysis of the host-plasmid effect" below). Genes also showing significant upregulation include AADC (key solvent formation enzyme), numerous histidine kinases (signaling pathways), glycolysis genes, electron transport genes, and pyruvate-formate lyase. Finally, both groES and groEL were upregulated at all three time points (1.8 to 14 fold higher).

Example 10

Transcriptional Analysis of the Host-Plasmid Interaction Effect

Comparison of the plasmid control strain, 824 (pSOS95del), to the wild type 824 strain reveals that the host-plasmid interaction is quite significant at the transcriptional level. SOM analysis resulted in the identification of 5 gene clusters. Four of the clusters represent sets of genes which have elevated expression in the 824(pSOS95del) plasmid control strain, while the fifth represents a cluster of genes which are down regulated. Many of the same trends are apparent in the plasmid control strain (when compared to the wild type) as were discussed above for the GroESL overexpressing strain (when compared to the plasmid control strain). Namely, many of the sporulation genes and flagellar and chemotaxis genes show early and enhanced expression. In addition, many of the heat shock proteins are upregulated early, suggesting the cells respond to the presence of a plasmid as they would to many other stresses. Several key metabolic genes were upregulated as well: an acid formation gene, butyrate kinase (buk); the solvent formation genes alcohol dehydrogenase (ADH) and acetoacetate decarboxylase (AADC); and several glycolytic genes, phosphofructokinase, GAPDH, triose phosphate isomerse, and a transcriptional regulator of sugar metabolism. Many response and transcriptional regulators are also upregulated. The gene cluster representing the downregulated genes includes hrcA (negative transcriptional regulator of chaperonin expression) and several primary metabolism genes. The inclusion of hrcA in the downregulated gene cluster would suggest that one would expect to see an upregulation of the chaperonins which it negatively regulates. We in fact see this with the presence of groES, groEL, and grpE genes in the upregulated gene clusters. Use of a priori gene regulation information provides for additional validation of the microarray data.

While the principles of this invention have been described in connection with specific embodiments, it should be understood clearly that these descriptions are added only by way of example and are not intended to limit, in any way, the scope of this invention. For instance, butanol and acetone have been described as the toxic organic molecules in this invention, but the methods and constructs described herein may be used to increase microorganism/cellular resistance to other toxic molecules or compounds including hexane derivatives and aromatic compounds like toluene as would otherwise be known to those skilled in the art for various solventogenic purposes or for application in other bioprocesses associated with such endeavors as bioremediation and biocatalysis. Other advantages, features and benefits will become apparent from the claims to be filed hereafter, with the scope of such claims determined by their reasonable equivalents, as would be understood by those skilled in the art.

We claim:

1. An isolated solventogenic bacterium having a recombinant plasmid comprising genetic code material to increase expression of a heat shock protein, said bacterium comprising a recombinant strain of solventogenic *Clostridia*.

2. The bacterium of claim 1 wherein said genetic material comprises a DNA sequence selected from the group consisting of the groE operon, the dnaK operon and combinations of said operons.

3. The bacterium of claim 1 wherein said genetic material comprises DNA encoding proteins selected from the group consisting of GroESL proteins, the DnaKJ proteins and combinations thereof.

4. The bacterium of claim 1 comprising constructed pSR1.

5. The bacterium of claim 1 comprising genetic code for expression of the GroESL heat shock proteins.

6. The bacterium of claim 5 comprising the pSOS95del shuttle vector and the groESL operon genes.

7. The bacterium of claim 6 wherein said plasmid comprises the pSOS95del shuttle vector and said bacterium is a recombinant strain of *C. acetobutylicum*.

8. A method of using expression of a heat shock protein to enhance solvent production, said method comprising:
   providing a recombinant solventogenic *C. acetobutylicum* bacterium, said bacterium transformed by a plasmid comprising genetic code to increase expression of a heat shock protein;
   providing a fermentation system conditioned for solvent production; and
   contacting said recombinant bacterium with said system over a time sufficient for expression of said heat shock protein and enhanced solvent production compared to production by said bacterium absent said transformation.

9. The method of claim 8 wherein said plasmid comprises genetic code for expression of the GroESL heat shock proteins.

10. A method of using expression of a heat shock protein to increase tolerance to a toxic substance, said method comprising:

provided a recombinant microorganism, said microorganism selected from recombinant strains of solventogenic *Clostridia, Aspergillus, Pichia*, species of the genus *Lactobacilli*, and species of the genus *Bacillus*, said microorganism transformed by a plasmid comprising genetic code to increase expression of a heat shock protein;

providing a fermentation system; and contacting said recombinant microorganism with said system over a time sufficient for expression of said heat shock protein said increased tolerance compared to tolerance of said recombinant microorganism absent said transformation.

11. The method of claim 10 wherein said recombinant strain comprises genetic code for expression of the GroESL heat shock proteins.

12. The method of claim 10 wherein contacting said recombinant microorganism with said system provides for bioremediation of a toxic substance.

13. The method of claim 10 wherein contacting said recombinant microorganism with said system provides for the biocatalysis of a target compound.

14. The method of claim 13 wherein said microorganism comprises a recombinant microorganism selected from the group consisting of recombinant microorganisms of the genus *Escherichia*, recombinant microorganisms of the genus *Saccharomyces*, and recombinant microorganisms of the genus *Pichia*.

15. A method of using expression of a heat shock protein to increase tolerance to solvent production, said method comprising:

providing a recombinant microorganism, said microorganism transformed by a plasmid comprising genetic code to increase expression of a heat shock protein providing a fermentation system; and contacting said recombinant microorganism with said system over a time sufficient for expression of said heat shock protein, said increased solvent tolerance compared to tolerance of said recombinant microorganism absent said transformation.

16. The method of claim 15 wherein said microorganism is selected from the group consisting of bacteria, yeast, and filamentous fungi.

17. The method of claim 15 wherein said microorganism comprises a recombinant strain of *C. acetobutylicum*.

18. The method of claim 15 wherein said microorganism is a recombinant bacterium species selected from the group consisting of species of the genus *Escherichia*, species of the genus *Lactobacilli* and species of the genus *Bacillus*.

19. The method of claim 17 wherein said recombinant strain comprises genetic code for expression of the GroESL heat shock proteins.

20. The method of claim 15 wherein contacting said recombinant microorganism with said system provides for bioremediation of a toxic substance.

21. The method of claim 20 wherein said microorganism comprises a recombinant species selected from the group consisting of species of the genus *Aspergillus*.

22. The method of claim 15 wherein contacting said recombinant microorganism with said system provides for the biocatalysis of a target compound.

23. The method of claim 22 wherein said microorganism comprises a recombinant microorganism selected from the group consisting of recombinant microorganisms of the genus *Escherichia*, recombinant microorganisms of the genus *Saccharomyces*, and recombinant microorganisms of the genus *Pichia*.

* * * * *

UNITED STATES PATENT AND TRADEMARK OFFICE
CERTIFICATE OF CORRECTION

| | |
|---|---|
| PATENT NO. | : 6,960,465 B1 |
| APPLICATION NO. | : 10/186335 |
| DATED | : November 1, 2005 |
| INVENTOR(S) | : Eleftherior T. Papoutsakis et al. |

It is certified that error appears in the above-identified patent and that said Letters Patent is hereby corrected as shown below:

<u>Column 4,</u>
Line 40, "Comillot" should be -- Cornillot --.

<u>Column 5,</u>
Line 59, "Hirayarna" should be -- Hirayama --.

<u>Column 7,</u>
Line 57, "Dnaj" should be -- DnaJ --.

<u>Column 8,</u>
Line 35, "Dnaj" should be -- DnaJ --.
Line 60, "8&91" should be -- 86&91 --.

<u>Column 9,</u>
Line 23, "Wiesenbom" should be -- Wiesenborn --.

<u>Column 11,</u>
Line 51, "stains" should be -- strains --.

<u>Column 15,</u>
Line 67, "72001" should be -- 7 2001 --.

<u>Column 19,</u>
Line 23, "700/o" should be -- 70% --.

UNITED STATES PATENT AND TRADEMARK OFFICE
CERTIFICATE OF CORRECTION

PATENT NO. : 6,960,465 B1
APPLICATION NO. : 10/186335
DATED : November 1, 2005
INVENTOR(S) : Eleftherior T. Papoutsakis et al.

It is certified that error appears in the above-identified patent and that said Letters Patent is hereby corrected as shown below:

Column 20,
Line 67, "32-fold" should be -- 3.2-fold --.

Signed and Sealed this

Twenty-seventh Day of June, 2006

JON W. DUDAS
*Director of the United States Patent and Trademark Office*